(12) United States Patent
Coetzee

(10) Patent No.: US 10,434,083 B2
(45) Date of Patent: Oct. 8, 2019

(54) TRANSMAMMARY DELIVERY OF CYCLOOXYGENASE-2 INHIBITORS FOR ANALGESIA IN NEONATES

(71) Applicant: Iowa State University Research Foundation, Inc., Ames, IA (US)

(72) Inventor: Johann F. Coetzee, Manhattan, KS (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 16/278,925

(22) Filed: Feb. 19, 2019

(65) Prior Publication Data

US 2019/0255010 A1 Aug. 22, 2019

Related U.S. Application Data

(60) Provisional application No. 62/632,327, filed on Feb. 19, 2018.

(51) Int. Cl.

| | | |
|---|---|---|
| *A61K 31/435* | (2006.01) | |
| *A61K 31/41* | (2006.01) | |
| *A61K 31/4245* | (2006.01) | |
| *A61K 31/426* | (2006.01) | |
| *A61K 31/415* | (2006.01) | |
| *A61K 31/40* | (2006.01) | |
| *A61K 31/38* | (2006.01) | |
| *A61K 31/335* | (2006.01) | |
| *A61K 31/341* | (2006.01) | |
| *A61P 29/02* | (2006.01) | |
| *A61K 9/00* | (2006.01) | |
| *A23K 50/30* | (2016.01) | |
| *A61K 31/13* | (2006.01) | |
| *A61K 31/42* | (2006.01) | |
| *A61K 31/4164* | (2006.01) | |
| *A23K 20/121* | (2016.01) | |

(52) U.S. Cl.
CPC .......... *A61K 31/341* (2013.01); *A61K 9/0019* (2013.01); *A61P 29/02* (2018.01); *A23K 20/121* (2016.05); *A23K 50/30* (2016.05); *A61K 31/13* (2013.01); *A61K 31/415* (2013.01); *A61K 31/4164* (2013.01); *A61K 31/42* (2013.01)

(58) Field of Classification Search
CPC .. A61K 31/435; A61K 31/41; A61K 31/4245; A61K 31/426; A61K 31/415; A61K 31/40; A61K 31/38; A61K 31/335
USPC ....... 514/277, 360, 364, 365, 403, 427, 430, 514/449

See application file for complete search history.

(56) References Cited

FOREIGN PATENT DOCUMENTS

WO    2014012117    1/2014

OTHER PUBLICATIONS

Bates, et al., "Translactational analgesia technology for the improvement of swine welfare during castration and tail docking", American Dairy Science Association, Community Choice Credit Union Convention Center, Mar. 17, 2014.
Pertzborn, et al., "Biological pain indicators for the characterization of piglet pain during and after processing", Swine Medicine Education Center, Poster, 2014.
Brown, et al., "Using 'translactational analgesia' to reduce piglet pain at castration", Centred on Swine, Sep. 2012.

*Primary Examiner* — Raymond J Henley, III
(74) *Attorney, Agent, or Firm* — Hovey Williams LLP

(57) ABSTRACT

Methods for transmammary administration of an analgesic to offspring swine are disclosed, which are useful for mitigating, inhibiting, and/or reducing pain in offspring swine prior to undergoing processing procedures that would cause or result in pain. The methods generally comprise administering, via injection, a cyclooxygenase-2 inhibitor class analgesic directly to a lactating female swine. The analgesic is passed indirectly to the offspring swine through the milk of the treated lactating female swine and has beneficial effects, including increases in weight gain, performance, and decreases in pain. A single dosage form injected into the lactating female is suitable for achieving indirect therapeutically effective levels of the cyclooxygenase-2 inhibitor class analgesic in the milk for the offspring.

21 Claims, 9 Drawing Sheets

TRANSMAMMARY DELIVERY OF CYCLOOXYGENASE-2 INHIBITORS FOR ANALGESIA IN NEONATES

CROSS-REFERENCE TO RELATED APPLICATIONS

The present application claims the priority benefit of U.S. Provisional Patent Application Ser. No. 62/632,327, filed Feb. 19, 2018, entitled TRANSMAMMARY DELIVERY OF CYCLOOXYGENASE-2 INHIBITORS FOR ANALGESIA IN NEONATES, incorporated by reference in its entirety herein.

BACKGROUND OF THE INVENTION

Field of the Invention

The present invention relates to improved techniques for pain management in swine processing.

Description of Related Art

Routine processing procedures carried out on piglets (e.g., castration, tail docking, teeth clipping, ear notching, etc.) are considered painful. There is increased negative public perception of such practices, and many have called for alleviation and mitigation of such painful procedures. The livestock industry is faced with significant challenges in formulating new animal welfare techniques related to these routine management practices, while remaining practical and cost-effective.

Previous work has focused on delivering a common NSAID, meloxicam, to piglets via the milk of medicated sows. However, these efforts were unsuccessful for various reasons. In some cases, the analgesic drug could not be delivered in the milk in high enough concentrations to achieve any pain relief in the piglets. In other cases, attempting higher dosages, minimal pain relief was observed, but only after administering 30 mg/kg bodyweight of meloxicam for 7 days (i.e., about 8,250 mg of meloxicam/treatment). Further, there was no observed improvement in growth or performance of the piglets. In fact, stomach ulcers were observed in several piglets, indicating potential lack of safety. Further, prolonged exposure to meloxicam would likely result in tissue residue in the treated animals, posing risks to meat consumers. Thus, these prior failed experiments have suggested that indirect delivery of analgesics via milk is not a feasible approach for pain relief in processing piglets.

SUMMARY OF THE INVENTION

The present invention is broadly concerned with methods for transmammary administration of an analgesic to an offspring swine. The methods comprise directly administering a therapeutically effective amount of a cyclooxygenase-2 inhibitor analgesic via injection to a lactating female swine, preferably as a single dosage, to yield a treated lactating female swine. Offspring swine are allowed to obtain milk from the treated lactating female swine, wherein the analgesic is passed indirectly to the offspring swine through the milk at levels to provide a therapeutic effect in the offspring swine.

Also described herein are methods of mitigating, inhibiting, and/or reducing pain in an offspring swine prior to undergoing processing procedures that would cause or result in pain. The methods comprise directly administering via injection a therapeutically effective amount of a cyclooxygenase-2 inhibitor analgesic to a lactating female swine to yield a treated lactating female swine. The offspring swine are allowed to obtain milk from the treated lactating female swine, wherein the analgesic is passed indirectly to the offspring swine through the milk at levels to provide a therapeutic effect in the offspring swine. The offspring swine are then subjected to processing, and will demonstrate reduced pain and discomfort as well as increased weight gain as compared to control offspring swine, i.e., those that did not obtain milk from the treated swine (or which obtained milk from an untreated swine).

DESCRIPTION OF THE INVENTION

Figure 1:
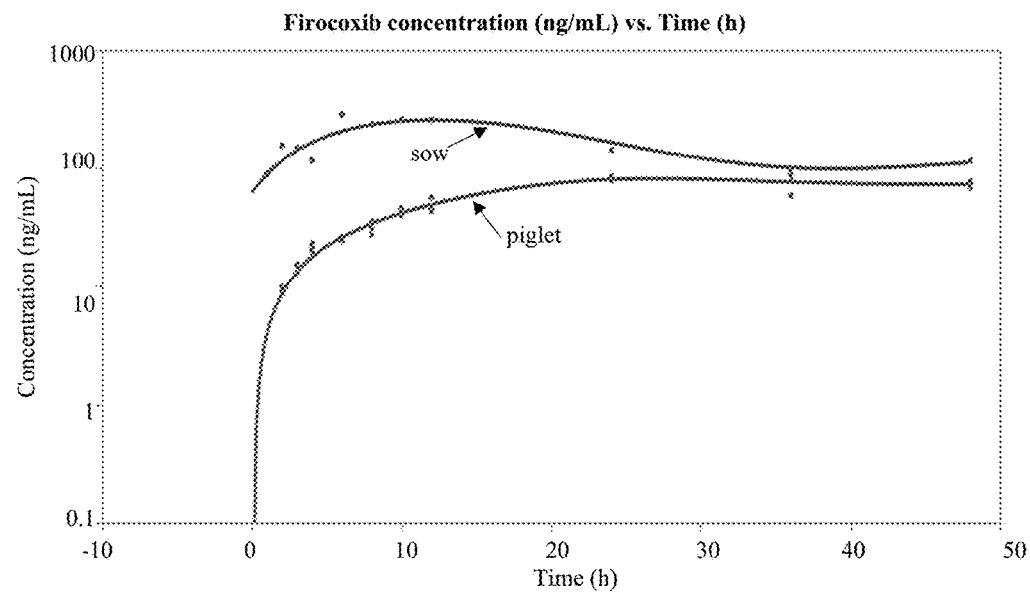
FIG. 1 is a graph of plasma firocoxib concentrations (ng/mL) over time in the lactating sow administered firocoxib via the intramuscular route at 1.5 mg/kg and nursing piglets in Example 1.

Despite these prior failures, described herein is a surprising and unexpected new approach for pain management in swine via transmammary delivery of a specific class of compounds, cyclooxygenase-2 inhibitors (aka coxibs). The worked carried out herein demonstrates and confirms successful transmammary delivery of a coxib for management of pain in swine following a single injection. Firocoxib (3-(cyclopropylmethoxy)-4-(4-(methylsulfonyl)phenyl-5, 5-dimethylfuranone) is representative of the coxib class of drugs, and the specific examples herein can be extended to other members of the coxib class including but not limited to Celecoxib, Rofecoxib, valdecoxib, mavacoxib, cimicoxib, robenacoxib, deracoxib, and pharmaceutically acceptable salts thereof.

In one or more embodiments, described herein are methods, systems, and processes for the indirect administration of an analgesic to offspring swine, particularly prior to processing. More specifically, the analgesic is administered to the piglet through translactational or transmammary delivery of the analgesic from a lactating female swine (sow). As used herein, "offspring" refers to young animals, and typically baby animals that are recently born (neonatal) and still nursing, it being appreciated that a particular offspring animal may not necessarily be the progeny or young delivered by the particular lactating sow from which it suckles in the inventive method. As used herein, "lactating female swine" refers a sow that produces or is expected to imminently produce milk for nursing young piglets.

The analgesic is administered directly to a lactating female swine via injection and passed indirectly to the offspring swine through the lactating sow's milk. The analgesic may be administered via subcutaneous, intramuscular, transdermal, or intravenous injection/administration. The analgesic can be administered to the lactating female swine individually or as part of a veterinary formulation comprising the analgesic and a carrier. The term "carrier," as used herein, means one or more compatible base compositions with which the analgesic is combined/dispersed to facilitate the administration of ingredient, and which is suitable for administration to an animal. For example, veterinary formulations include liquid systems suitable for injection, and include carriers such as aqueous solutions, glycerol, polyethylene glycol, and the like. Such preparations may also routinely contain salts, buffering agents, saline, preservatives, and optionally other therapeutic ingredients or active agents. The carrier would naturally be selected to minimize any degradation of the active ingredient and to minimize any adverse side effects in the subject, as would be well known to one of ordinary skill in the art. As used herein, a pharmaceutically acceptable "salt" of the invention includes acid addition salts. The term "pharmaceutically acceptable," as used herein, is meant to include compounds that are not biologically or otherwise undesirable, i.e., the compound may be administered without causing any undesirable biological effects or interacting in a deleterious manner or interfering with any of the other components of the composition in which it is contained.

It will be appreciated that the offspring swine (i.e., piglet) preferably suckles and obtains the milk directly from the lactating female; however, it will be understood that the lactating female swine could also be milked to obtain milk containing the analgesic, which can then be fed to the offspring swine (e.g., in a bottle). The amount of analgesic administered via injection to the lactating female swine is an amount sufficient to provide a therapeutically effect dosage of the analgesic in the milk for each offspring swine.

In one or more embodiments, techniques of the invention involve successful delivery of analgesic drug to piglets nursing on directly medicated sows following a single administration (injection) of a therapeutically effective dosage of from about 1 mg/kg to about 5 mg/kg of coxib, preferably from about 1 mg/kg to about 3 mg/kg of coxib, more preferably from about 1 mg/kg to about 2 mg/kg of coxib, and even more preferably about 1.5 mg/kg based upon the bodyweight of sow to which the coxib is directly administered. Thus, it will be appreciated that in the case of coxib salts, for example, the coxib formulation may be administered in amounts greater than the above ranges to provide sufficient levels of the active coxib. It will be appreciated that the proposed dose is substantially less than the daily dose of other analgesics and only requires a single administration rather than repeated dosage regimens required to achieve therapeutically effective levels in the milk with other analgesics. It is further noted that our data demonstrates that increasing the sow dose beyond 2 firocoxib mg/kg does not appear to increase the therapeutically effective amount of drug available in the milk; however, additional reasonable dosages are included herein and should not be interpreted as being excluded unless noted. As used herein, a "therapeutically effective amount" or "concentration" refers to an amount capable of providing bioavailable levels of the active agent sufficient to achieve the desired effect (e.g., analgesia) in the offspring swine.

In one or more embodiments, techniques of the invention further involve increasing piglet weight gain and performance after nursing on sows that received firocoxib. Specifically, treated piglets unexpectedly have improved growth (Average daily gain (ADG)) when suckling from sows treated with firocoxib as compared to control piglets suckling from untreated sows (regardless of processing status). In one or more embodiments, techniques of the invention further involve reduction of stress (cortisol response) in piglets following transmammary delivery of firocoxib in piglets nursing on medicated sows after receiving a single injection of the drug. Unexpectedly, the indirect delivery of the analgesic appears to be more effective at improving piglet performance than direct administration of analgesics to the piglets.

In one or more embodiments, the inventive system is particularly advantageous for mitigating, inhibiting, and/or reducing pain in an offspring swine prior to undergoing processing procedures that would cause or result in pain. Processing includes various routine procedures carried out as part of animal management and husbandry. As used herein, "processing" includes castration, branding, docking (tail or ears), teeth clipping, and identification tagging or implanting of the offspring animal. Pain is defined as an aversive sensory or emotional experience representing awareness by the animal of actual or potential tissue damage. Pain is associated with physiological, behavioral and neuroendocrine changes aimed at reducing or avoiding tissue damage, limiting pain reoccurrence and promoting recovery. In the invention, a therapeutically effective amount of the analgesic is indirectly delivered to the offspring swine, as described above, at a given time point prior to subjecting the swine to the painful processing event. As such, the direct dosage of the analgesic is preferably administered via injection to the lactating female swine at a designated time point (or range) prior to the painful processing event, such that effective levels of the analgesic are achieved in the offspring swine prior to, during, and/or after the painful processing event, such that pain perception by the treated offspring swine is mitigated, inhibited, or otherwise lessened. In one or more embodiments, the analgesic is administered via injection directly to the lactating swine about 0.5 hours to about 96 hours prior to subjecting the offspring to processing, preferably from about 2 hours to about 24 hours prior, and more preferably from about 4 hours to about 12 hours prior to subjecting the offspring to processing. Preferably, the analgesic accumulates in the milk to reach a therapeutically effective indirect dosage amount of analgesic about 6 hours after injection into the sow.

For example, cortisol levels will be suppressed in the indirectly treated offspring, as compared to offspring subjected to processing without indirectly receiving the analgesic. Similarly, untreated offspring swine will have a perceivable reduced skin temperature, whereas treated offspring swine will maintain normal skin temperature ranges after processing. Furthermore, piglets nursing on medicated sows are expected to express fewer related pain behaviors including, but not limited to, alterations in gait (stride length, contact area, contact pressure, force and impulse) or changes in facial expressions assessed using a facial grimace scale.

Advantageously, the invention may help avoid the need for other pain mitigation techniques (which can themselves be stressful to the animal), such as the use of a local anesthetic (e.g., lidocaine, procaine, or systemic sedative analgesia) or other adjunctive therapy (e.g., antibiotic, hormonal implant, ionophore, other growth promotants, or vaccine) in conjunction with the painful processing event.

In one or more embodiments, techniques of the invention further involve a preferred timeline for the injection of the analgesic (firocoxib) to the sow and the conducting the painful procedure in the piglets to optimize the analgesic effects after transmammary delivery.

Techniques of the invention advantageous achieve the foregoing benefits, while avoiding stomach ulcers in the sows and/or piglets, as well as any accumulation of the drug in the animal's tissue. This suggests that the proposed practices are safe not only for the animals, but pose a minimal risk of meat residues that would potentially pose a risk to the consumer.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Pharmacokinetics and Transmammary Delivery of Firocoxib in a Single Sow and her Litter The objective of this study was to characterize the pharmacokinetic profile and transmammary delivery of firocoxib in a single sow and her litter when administered via injection to provide analgesia to piglets via the milk prior to routine piglet processing procedures. One crossbred sow and her litter sourced from the MVS-Klitz Farm was used for this project. The sow was in good health, and had not received treatment with anti-inflammatory drugs by any route. The study sow was housed in a farrowing crate. Feed and water was provided ad libitum throughout the study period. No additional medications were provided. Study animals were identified using unique duplicate ear tags and/or tattoos.

There was one treatment group in this study (refer to Table 1). The sow was given firocoxib (20 mg/mL) on Study Day 0. Firocoxib was administered via injection five (+/−2) days post-farrow, at 1.5 mg/kg IM.

TABLE 1

| Treatment Group | No of Animals | Body-weight | Treatment Administration Route | Dose Administration | Dose Volume |
|---|---|---|---|---|---|
| Firocoxib | 1 | 241 kg | Intramuscular | 1.5 mg/kg | 18.1 mL |

Blood (sodium heparin tubes) was collected from the sow via jugular venipuncture at the following time points after drug administration via injection to the sow: 0, 1, 2, 3, 4, 6, 8, 10, 12, 24, 36 and 48 hours. The piglets had blood collected via jugular venipuncture at the following timepoints following sow drug administration via injection:

Piglets 1-3 was bled at times 0, 3, 8 and 24 hours
Piglets 4-6 was bled at times 1, 4, 10 and 36 hours
Piglets 7-9 was bled at times 2, 6, 12 and 48 hours.

Approximately 10 mL of blood was collected from the sow at each time point, and approximately 5 mL was collected from each piglet at each time point. Following blood collection at the 48 hour time point, the sow and piglets was euthanized and disposed of per study site procedures.

Samples were stored on ice after collection and before processing. Blood samples were centrifuged for 10 minutes at 1,500 g. Collected plasma was placed in duplicate cryovials with a single-use transfer pipette and frozen at −70° C. until analysis. Cryovials were labeled with the time point and collection date.

Plasma concentrations of firocoxib were measured with high-pressure liquid chromatography-tandem mass spectrometry (Shimadzu Prominence, Shimadzu Scientific Instruments, Columbia, Md., USA). Briefly, frozen samples or standards were thawed at room temperature and rigorously vortexed once completely thawed. A 200 µL plasma sample was added to 400 µL 5% Acetic Acid and the internal standard celecoxib (20 µg/mL). The entire diluted sample was added to a 3 mL solid phase extraction tubes (OASIS) which was conditioned prior with methanol (2 ml) and equilibrated with water (2 ml). The sample was then gravity filtered through the solid phase extraction tubes and subsequently washed with 1 ml 5% acetic acid, followed by 1 ml solution of 25% methanol/75% water. Using 2×0.75 mL acetonitrile, firocoxib was eluted into a glass tube and an additional internal standard piroxicam (10 ng/µL) was added. Samples were evaporated to dryness at 48° C. under a stream of nitrogen, reconstituted with 200 acetonitrile 25% in water and pipetted into an injection vial for LC-MS/MS analysis with the injection volume set to 10 µL. The mobile phase consisted of acetonitrile and formic acid (0.1%) at a flow rate of 0.4 mL/min. The concentration of this mobile phase began at 85% formic acid (0.1%) from 0 to 0.5 minutes with a linear gradient to 50% formic acid (0.1%) at 2.5 minutes, which was maintained until 3 minutes, followed by a linear gradient to 85% formic acid (0.1%) at 4 minutes with a total run time of 5 minutes.

Separation was achieved with a $C_8$ column maintained at 40° C. The standard curve of firocoxib concentration determined using porcine plasma was linear from 0.020 to 5.0 µg/mL and was accepted when the correlation coefficient exceeded 0.99 and measured values were within 15% of the actual values. The lower limit of quantification, defined as the lowest concentration on a linear standard curve with predicted concentrations within 15% of the actual concentration, was 0.020 µg/mL.

Firocoxib time concentration data was analyzed using a commercially available computer software program (Kinetica, Thermo Scientific). The pharmacokinetic profile in the sow is summarized in Table 2.

TABLE 2

Pharmacokinetic profile of firocoxib in sow and nursing piglets.

| Parameter | Unit | Value |
|---|---|---|
| Dose (IM) | mg | 361.50 |
| $C_{max}$ | ng/mL | 287.10 |
| $T_{max}$ | h | 6.0 |
| $AUC_{last}$ | µg/mL * h | 7.46 |
| $AUC_{extra}$ | µg/mL * h | 3.68 |
| $AUC_{tot}$ | µg/mL * h | 11.14 |
| % $AUC_{extra}$ | % | 33.02 |
| $AUMC_{last}$ | µg/mL * $(h)^2$ | 155.18 |
| $AUMC_{extra}$ | µg/mL * $(h)^2$ | 322.22 |
| $AUM_{tot}$ | µg/mL * $(h)^2$ | 477.39 |
| $T_{1/2}$ | h | 27.46 |
| MRT | h | 42.86 |
| Clearance | L/h | 32.45 |
| $V_z$ | L | 1285.61 |
| $V_{ss}$ | L | 1390.95 |
| $MRT_{last}$ | h | 20.80 |

Firocoxib in the sow was rapidly absorbed after IM administration achieving a peak concentration of 287.10 ng/mL at 6 hours after treatment. Firocoxib also demonstrated an exceptional volume of distribution and long plasma elimination half-life.

The pharmacokinetic profile of firocoxib in the piglets relative to the sows after transmammary delivery is presented in FIG. 1.

Figure 2:
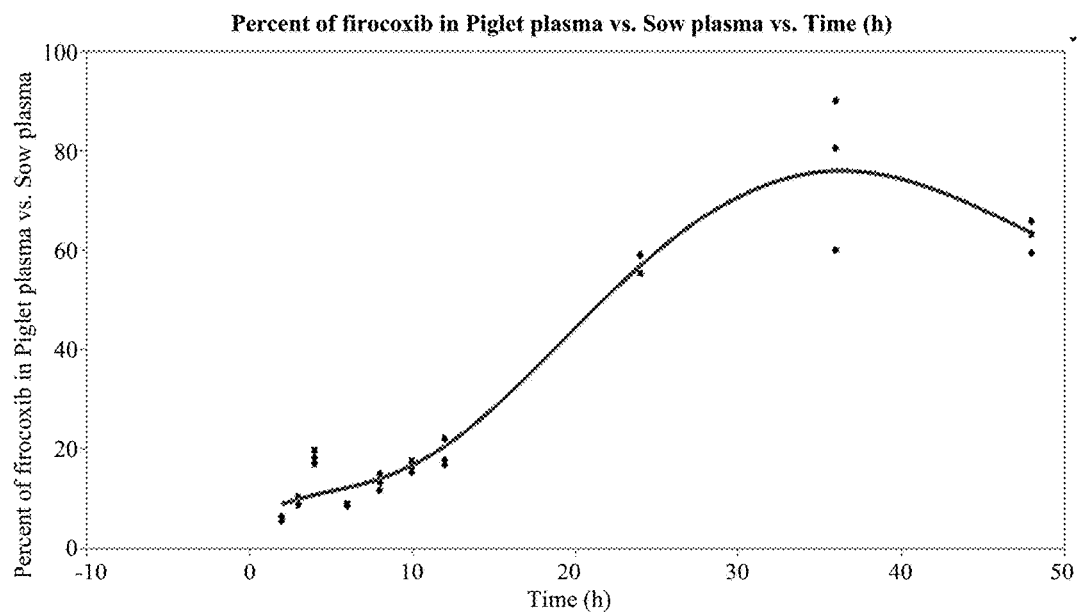
FIG. 2 is a graph comparing the percentage of firocoxib detected in piglet plasma as compared to sow plasma over time in Example 1.

Firocoxib was readily transferred into the milk of the sow as reflected by plasma drug concentrations that were maintained above 10 ng/mL from 2 hours post-exposure to milk from a treated sow to the end of the study. There was also evidence of significant dose accumulation as evidenced by the maintenance of steady state concentrations from 10 hours to the end of the study. The amount of plasma firocoxib in piglets expressed as a percentage of the sow plasma concentrations steadily increased over the course of the study as illustrated in FIG. 2.

In conclusion, the results of this pilot study demonstrate that firocoxib has a very high volume of distribution in sows resulting in significant transmammary delivery and dose accumulation in suckling piglets. These data suggest that firocoxib may provide effective analgesia in suckling piglets after tail docking and castration following intramuscular injection to the lactating sow.

Example 2

Pharmacokinetics and Transmammary Delivery of Firocoxib to Piglets after Intramuscular Administration to Sows In this Example, the impact of transmammary delivered firocoxib on the pain response and performance of piglets after traditional processing procedures (castration, tail docking and teeth clipping) was examined along with the drug residue depletion profile of firocoxib in sows and piglets to ensure that extra-label drug use complies with the requirements of the Animal Medicinal Drug Use Clarification Act (1994) (AMDUCA).

Materials and Methods

Protocols involved intramuscular injection of Firocoxib to lactating sows at either 0.5, 1.0, 1.5 or 2 mg/kg, and analysis in sows and select piglets at 21 days post treatment. Pregnant Yorkshire×Landrace sows (mean±SEM bodyweight, 250.3±7.61 kg) that were approximately 1 week before farrowing were sourced from a commercial swine farm. Each sow was examined by a veterinarian to confirm that she was healthy and pregnant. A unique numerical ear tag (Allflex Global Ear Tags, Allflex USA, Inc., DFW Airport, TX) was placed in the right ear of each sow for identification. The sows were housed in a commercial swine operation at MVS (West Point, Nebr.) in accordance with the recommendations in the Guide for the Care and Use of Agricultural Animals in Agricultural Use and Research and Teaching (Guide for the Care and Use of Agricultural Animals in Agricultural Research and Teaching, 2010). Sows were placed in Quad- or Euro-style farrowing stalls (Thorp Equipment, Thorp, Wis.), depending on availability. Regardless of stall type, each sow was housed in a farrowing crate measuring 0.6 m×2.1 m. Quad and Euro crates had piglet creep areas of 7.0 $m^2$ and 6.4 $m^2$, respectively. After farrowing, a heat lamp was provided on one side of the creep area for the piglets in each crate. All sows were fed a diet that met or exceeded National Research Council (NRC, 2012) nutrient requirements and water was provided ad libitum. Each litter provided at least six male and three female piglets for sampling with the exception of one sow that had 5 males and 4 females in the litter, and one sow that had 3 males and 6 females in the litter. Piglets were clinically examined and weighed on Study Day 0 prior to dosing. Cross fostering of the litters was permitted. Bodyweights were used to randomly assign sows to 1 of 4 treatment groups (n=4 sows/group) as detailed in Table 3.

A sample size of 4 sows was selected to describe the pharmacokinetics of firocoxib. For the comparison of plasma cortisol concentrations and average daily gain in bodyweight (ADG), a sample size of 36 piglets/treatment group was calculated to provide Statistical Power of 0.8 assuming an alpha of 0.05, sigma of 0.54 and delta of 0.20. At the time of study commencement (T0), sows received a single dose of firocoxib (Equioxx Injection, Merial, Duluth, Ga.) (Lot number 4VP07, Expiration Date November 2017) administered at either 0.5 mg/kg, 1.0 mg/kg, 1.5 mg/kg, or 2.0 mg/kg by IM injection into the right lateral neck using an 18-gauge, 1.5-inch needle attached to a 20-mL syringe (Table 3). In cases where the calculated dose volume exceeded 20-mL, the remaining volume was administered via IM injection in the left lateral neck muscle.

used for manual restraint of each sow in her crate. The blood samples (2 mL/sample) from the piglets were collected from the left or right cranial vena cava using a 3.8-cm, 20-gauge hypodermic needle (TycoHealth Care, Mansfield, Mass.) attached to a 3-mL syringe (TycoHealth Care, Mansfield, Mass.). Physical restraint of the piglet was achieved by placing the animal in a supine position during sample collection. Blood samples were transferred to 6-mL evacuated tubes that contained lithium heparin (Vacuette plasma tubes, Greiner Bio-One, Monroe, N.C.) that were stored on ice for up to 2 h before processing. The blood samples were centrifuged for 10 min at 1,500×g. The plasma was then removed, placed in cryovials, and frozen at −80° C. until analysis.

On Day −1 or Day 0, approximately 3 mL of blood was collected by jugular venipuncture from all sows and piglets for determination of baseline PGE2 and Firocoxib concentrations. Prior to sow dosing, the piglets had body weight data collected.

On Day 0, the pharmacokinetic portion of the study commenced. The test article was administered intramuscularly in the right neck to sows. Blood samples for Firocoxib determination were collected by jugular venipuncture from sows and 3 piglets/litter (2 male and one female at each timepoint) at 0, 2, 4, 6, 8, 12, 24, 48, 72, 96 and 120 hours after drug injection in the sow.

Castration, teeth clipping, and tail docking were completed for each male piglet between the 6-h and 8-h blood collection time points. Female piglets did not undergo any of these procedures and thus served as procedural controls.

TABLE 3

Study population information and doses of firocoxib administered to lactating sows via intramuscular injection at 0.5 mg/kg, 1.0 mg/kg, 1.5 mg/kg, or 2.0 mg/kg bodyweight.

| Sow treatment group | Parity | Weight, kg | Number of piglets/litter Male | Female | Preweaning piglet deaths | Sow Dose, mg | Dose volume administered to sows IM (mL) |
|---|---|---|---|---|---|---|---|
| #1 | 8 | 266 | 6 | 3 | 0 | 133 | 6.5 |
| 0.5 mg/kg | 7 | 255 | 6 | 3 | 1 | 127.5 | 6.5 |
|  | 5 | 238 | 6 | 3 | 0 | 119 | 6.0 |
|  | 1 | 179 | 5 | 4 | 1 | 89.5 | 4.5 |
| Total |  |  | 23 | 13 | 2 |  |  |
| Mean | 5.25 | 234.5 |  |  |  | 117.25 | 5.88 |
| SEM | 1.55 | 19.38 |  |  |  | 9.69 | 0.47 |
| #2 | 9 | 211 | 6 | 3 | 0 | 211 | 10.5 |
| 1.0 mg/kg | 9 | 292 | 6 | 3 | 1 | 292 | 14.5 |
|  | 8 | 258 | 6 | 3 | 2 | 258 | 13.0 |
|  | 4 | 241 | 6 | 3 | 0 | 241 | 12.0 |
| Total |  |  | 24 | 12 | 3 |  |  |
| Mean | 7.5 | 250.5 |  |  |  | 250.5 | 12.5 |
| SEM | 1.19 | 16.90 |  |  |  | 16.90 | 0.84 |
| #3 | 7 | 292 | 6 | 3 | 0 | 438 | 22.0 |
| 1.5 mg/kg | 4 | 248 | 6 | 3 | 2 | 372 | 18.5 |
|  | 6 | 260 | 6 | 3 | 1 | 390 | 19.5 |
|  | 2 | 224 | 3 | 6 | 0 | 336 | 17.0 |
| Total |  |  | 21 | 15 | 3 |  |  |
| Mean | 4.75 | 256 |  |  |  | 384 | 19.25 |
| SEM | 1.11 | 14.14 |  |  |  | 21.21 | 1.05 |
| #4 | 10 | 262 | 6 | 3 | 0 | 524 | 26.0 |
| 2.0 mg/kg | 8 | 294 | 6 | 3 | 0 | 588 | 29.5 |
|  | 6 | 253 | 6 | 3 | 0 | 506 | 25.5 |
|  | 2 | 231 | 6 | 3 | 0 | 462 | 23.0 |
| Total |  |  | 24 | 12 | 0 |  |  |
| Mean | 6.5 | 260 |  |  |  | 520 | 26 |
| SEM | 1.71 | 13.07 |  |  |  | 26.14 | 1.34 |

Blood samples for firocoxib determination were collected from the sows and three piglets/litter (two male and one female piglet at each time point) at 0, 2, 4, 6, 8, 12, 24, 48, 72, 96, and 120 h post-drug injection to the sow. The blood sample from each sow (8 mL/sample) was collected via the left or right jugular vein using a 25.4-mm, 16-gauge hypodermic needle (Air-Tite Products, Virginia Beach, Va.) attached to a 12-mL Luer-Lok syringe (TycoHealth Care, Mansfield, Mass.). During blood collection, a pig snare was Castration was performed using a number 10 scalpel blade to making two vertical incisions approximately 2-3 cm long in the skin covering the testicles. The testicles were then marsupialized, and manual pressure was applied to the spermatic cord until it separated from the piglet's body. Side-cutter pliers were used to remove the tail at the $6^{th}$ coccygeal vertebral body, and the canine teeth were filed flush with the gingival tissue.

On day 21 post-drug injection in the sow, the body weight of each sow and piglet was recorded before weaning to calculate average daily weight gain.

Thereafter, sows and piglets in all groups were humanely euthanized and examined for macroscopic signs of NSAID toxicity. Necropsies were performed on all animals to inspect for macroscopic signs of NSAID toxicity. Samples of kidney, liver, small intestine and stomach were sectioned into 0.5-1 cm slices and placed in plastic jars containing 10% buffered formalin in a 10:1 formalin:tissue ratio for histopathology examination. Approximately 200 g of muscle, liver, kidney, fat, and injection site tissue were also collected from each sow for firocoxib residue determination. The liver, the two kidneys, and 50 g muscle and fat were collected from at least three piglets/litter (two male and one female) for tissue drug residue determination. The tissue samples were stored at −20° C. until analysis.

Firocoxib in Plasma

Plasma concentrations of firocoxib were determined using high-pressure liquid chromatography (Agilent 1100 Pump, Column Compartment and Autosampler, Agilent Technologies, Santa Clara, Calif., USA) with mass spectrometry detection (LTQ Ion Trap, Thermo Scientific, San Jose, Calif., USA). Briefly, frozen samples or standards were thawed at room temperature and rigorously vortexed once completely thawed. Plasma samples, plasma spikes, plasma QC's, and blanks, 100 were protein precipitated in 1.5 mL microcentrifuge tubes with 400 µL of acetonitrile/0.1% formic acid. Plasma samples, plasma spikes, plasma quality control samples, and blanks (100 µL) were then protein-precipitated in 1.5-mL microcentrifuge tubes with 400 µL acetonitrile/0.1% formic acid. A d6-firocoxib internal standard was incorporated into the acetonitrile precipitating agent at a concentration of 200 ng/mL. The samples were vortexed for 5 seconds after addition of the acetonitrile and centrifuged for 20 min at 3,773×g to sediment the protein pellet. Following centrifugation, the supernatant was poured into cell culture tubes and evaporated to dryness in a Turbovap concentration evaporator at 48° C. The tube contents were reconstituted with 150 µL 25% acetonitrile and transferred to autosampler vials equipped with 300-µL glass inserts. The samples were centrifuged at 770×g before liquid chromatography-mass spectroscopy (LC-MS) analysis.

Twelve calibration spikes were prepared in blank porcine plasma in the concentration range of 1-5,000 ng/mL for the samples from the sows. The samples from the piglets were analyzed using a narrower range of calibration spikes of 1-500 ng/mL. A linear (1/X) fit was used for the piglet plasma samples and the narrower 1-500 ng/mL concentration range. A quadratic (1/X) fit was used for the sow plasma samples and the 1-5,000 ng/mL concentration range.

Firocoxib in Tissues

Tissue concentrations of firocoxib and its descyclopropylmethyl metabolite were determined using high-pressure liquid chromatography (Agilent 1100 Pump, Column Compartment and Autosampler, Agilent Technologies, Santa Clara, Calif., USA) with mass spectrometry detection (LTQ Ion Trap, Thermo Scientific, San Jose, Calif., USA). The tissue samples analysed were muscle, injection site, kidney, liver, and fat. Eight calibration spikes were prepared in blank porcine tissue in the concentration range of 0.05-10 µg/g. The tissue samples were thawed and homogenized in a Waring blender before extraction and analysis. The tissue samples, tissue spikes, blanks, and 1 gram tissue homogenate were extracted using 10 mL of a 4:1 mixture of acetonitrile:water in a 50-mL centrifuge tube. An internal standard (d6-firocoxib) of 25 µL of a 100 ng/µL solution was added to the tissue homogenate before extraction. The solvent extraction was performed on a multi-tube vortex mixer for 15 min after the addition of the acetonitrile mixture. The extracted samples were then centrifuged for 5 min at 1,000×g and filtered through glass fiber filters into 15 mL centrifuge tubes. Finally, 1 mL of each extract was pipetted into cell culture tubes and evaporated to dryness at 48° C. using a Turbovap concentration evaporator. The tube contents were reconstituted with 150 µL 25% acetonitrile and transferred to autosampler vials equipped with 300-µL glass inserts. The samples were centrifuged at 770×g before LC-MS analysis.

Firocoxib Plasma and Tissue Analyses

Plasma and tissue firocoxib concentrations were determined using high-pressure liquid chromatography (Agilent 1100 Pump, Column Compartment and Autosampler, Agilent Technologies, Santa Clara, Calif.) with mass spectrometry detection (LTQ Ion Trap, Thermo Scientific, San Jose, Calif.). A 25-µL injection volume was used for the LC-MS analysis. The mobile phases were A (0.1% formic acid in water) and B (0.1% formic acid in acetonitrile), at flow rates of 0.275 mL/min. The mobile phase began at 25% B with a linear gradient to 95% B in 5 minutes that was maintained for 1.25 min at 0.325 mL/min, followed by re-equilibration to 25% B. Separation was achieved with a HypersilGoldC18 column (100 mm×2.1 mm, 3 µm particles, Thermo Scientific, San Jose, Calif.) maintained at 50° C. Firocoxib and d6-firocoxib each eluted at 4.9 min. Full scan MS was used for analyte detection and three fragment ions were used for quantitation of each analyte species. The fragment ions for firocoxib were at 283, 265, and 237 m/z; fragment ions at 289, 270, and 243 m/z were characteristic of d6-firocoxib fragmentation. The descyclopropylmethyl metabolite produced a single fragment ion at 209 m/z. Firocoxib and d6-firocoxib were analyzed in positive ion mode. The mass spectrometer was optimized for detection of firocoxib using infusion of a firocoxib solution (10 µg/mL) into the mobile phase of 80% B. Detection of firocoxib was enhanced with a transfer capillary temperature of 350° C.

The blank (porcine plasma), calibration spike, QC, and porcine samples were batch processed for sequencing using a processing method developed in the Xcalibur software application (Thermo Scientific, San Jose, Calif.). The processing method automatically identified and integrated each peak in each sample and calculated the calibration curve based on a weighted (1/X) quadratic or linear fit. Firocoxib concentrations in unknown samples were calculated based on the relevant calibration curve using the Xcalibur software. Results were then viewed in the Quan Browser portion of the Xcalibur software.

For plasma samples, the calibration curves had correlation coefficients ($R^2$) exceeding 0.995 across the concentration range. The QC samples at 7.5, 15, 35, 75, 150, and 1,500 ng/mL were within a tolerance of ±15% of the nominal value. The limit of quantitation of the analysis was 1.0 ng/mL, with a limit of detection of 0.2 ng/mL. For tissue samples, calibration curves had correlation coefficients ($r^2$) exceeding 0.99 across the concentration range. The limit of quantitation of the analysis for both firocoxib and the descyclopropylmethyl metabolite was 0.05 μg/g; the limit of detection was 0.01 μg/g.

Histopathology Examination

Formalin-fixed sections of kidney, liver, small intestine and stomach from sows and 3 piglets/litter were trimmed and positioned in cassettes loaded into an automated tissue processor (Sakura VIP 5, Sakura Finetek, Torrance, Calif.) for overnight paraffin infiltration. Processed tissues in cassettes were then placed in a paraffin bath (Sakura Tissue-Tek TEC 5, Sakura Finetek, Torrance, Calif.) after which they were removed from the cassette and oriented in molds. The paraffin-embedded tissues were then fully exposed through sectioning on a microtome (HM 355S Automatic Microtome, Thermo Fisher, Waltham, Mass.). Tissue sections were cut at 4 microns from the cooled blocks. Paraffin ribbons with tissue were then laid out on a water bath and the floating tissue sections were collected onto microscope slides. The unstained tissue sections were then mounted on the slide and dried at 60° C. for 20 minutes. Finally, the tissue was deparaffinized and rehydrated for staining by transfer through xylene and a series of decreasing concentrations of alcohol to hematoxylin on an automated stainer (Sakura Tissue-Tek Prisma, Sakura Finetek, Torrance, Calif.). After a tap water rinse, the tissue on the slide was counterstained with eosin, dehydrated in an alcohol series, cleared in xylene and cover slipped (Sakura Tissue-Tek Glas g2) prior to histological examination by a veterinary diagnostician with experience in the histological examination of swine tissues.

Plasma Cortisol Concentrations

To accommodate blood volume restrictions, blood samples for cortisol determination were collected from three randomly selected piglets/litter (two male and one female piglet at each time point) prior to processing (6 h after firocoxib injection in the sow) and after processing at approximately 8, 12, 24, 48, 72, 96 h after drug injection in the sow. These time points corresponded to approximately 0, 2, 6, 18, 42, 66 and 90 h after processing. The blood for cortisol analysis was collected in 3-mL heparinized blood collection tubes (BD Vacutainer, Franklin Lakes, N.J.) and then centrifuged for 10 min at 1,500×g. The plasma was collected, then immediately frozen and stored at −80° C. The analyses for plasma cortisol concentrations were performed within 60 d after sample collection and within 10 consecutive days once the analyses were started. Plasma cortisol concentrations were determined using a commercial radioimmunoassay kit (CortiCote I-125, MP Biomedicals, Santa Ana, Calif.). The samples were incubated at 4° C. for 2 h to improve assay sensitivity. The samples were processed in duplicates and the processing was repeated if the difference between paired samples in cortisol concentrations were more than 15%. The assay had a detection range of 0.64-150 ng/mL. The coefficient of variation for the intra-assay variability was 9.33%. The inter-assay variability was 10.58%.

Pharmacokinetic Analysis of Data

The firocoxib plasma concentration versus time profile from each sow of four treatment groups treated intramuscularly with firocoxib at dose of 2 mg/kg, 1.5 mg/kg, 1 mg/kg and 0.5 mg/kg, were subjected to PK analysis using commercially available software (Phoenix® Win-Nonlin® 7.0, Certara, Inc. Princeton, N.J., USA). The data were analyzed using non-compartmental methods implemented in the software with Model Type Plasma (200-202) with uniform weighting. The PK parameters determined were: elimination rate constant ($\lambda_z$, slope of the terminal phase), terminal half-life ($T_{1/2\ \lambda z}$), maximum plasma concentration ($C_{max}$); time to achieve peak concentration ($T_{max}$), area under the concentration time curve (AUC), area under the first moment of the concentration-time curve (AUMC), apparent volume of distribution during the elimination phase ($V_z/F$) and apparent systemic clearance (CL/F) and mean residence time (MRT). The rate constant ($\lambda_z$) associated with the terminal phase was calculated using mean values and linear regression of the terminal part of the log plasma concentration vs. time curve.

The Linear Trapezoidal Linear Interpolation method was used to determine AUC and AUMC. For the calculation of $AUC_{0-last}$ and $AUMC_{0-last}$, time range from the first measurement to the last measurement of drug concentration, as well as the extrapolation to infinity ($AUC_{0-\infty}$, $AUMC_{0-\infty}$) was used. AUC and AUMC values were extrapolated to infinity to account for the total sow exposure to firocoxib.

For each treatment, plasma firocoxib concentrations versus time data of piglets (n=36 per treatment) were subjected to non-compartment analysis using sparse data option available in the software (Phoenix® WinNonlin® 7.0, Certara, Inc. Princeton, N.J., USA). The pharmacokinetic parameters $\lambda_z$, $T_{1/2}\lambda$ z, $C_{max}$, $T_{max}$, AUC, AUMC, and MRT were estimated as described for the sows. The non-compartment analysis (NCA) sparse method calculates pharmacokinetic parameters based on the mean profile for all the subjects in the dataset. Therefore, in this analysis, the standard error of the mean was calculated only for $T_{max}$, $C_{max}$ and $AUC_{0-last}$.

The relative transfer of firocoxib from medicated sows to piglets was evaluated by comparing the piglet plasma drug concentration as a percentage of the sow plasma drug concentration at each time point. Total piglet exposure to firocoxib via milk consumed from treated dams was evaluated by comparing the firocoxib AUC for the piglets with the drug AUC calculated for the corresponding dams from each treatment. Exposure percentages were determined using the equation:

$$\% \text{ Exposure} = 100 \times \frac{AUC(\text{piglet})}{AUC(\text{sow})}$$

Statistical Analysis

Data were entered into a commercial software program for analysis (Microsoft Excel, Redmond, Wash.). Firocoxib pharmacokinetic parameters were not normally distributed. Therefore, the pharmacokinetic outcomes were compared statistically using Wilcoxon Rank Sum tests (JMP Pro. 13.0, SAS Institute, Cary, N.C.). Initial analysis examined the impact of piglet gender on plasma firocoxib concentration to determine if data from male and female piglets could be pooled for the subsequent pharmacokinetic analysis. Thereafter pharmacokinetic outcomes were compared using non-parametric methods. Dose linearity was investigated by calculating the square of the Pearson correlation coefficient ($R^2$) for linear regression. Statistical significance for all pharmacokinetic outcomes was set a priori at $P<0.05$.

Plasma cortisol concentrations and ADG were analyzed using a nonlinear mixed-effects analysis incorporating both fixed effects and random effects (PROC GLMMIX; SAS university edition v9.04.01, SAS Institute, Cary, N.C.). The population cortisol concentrations best fit a lognormal model. Time, treatment and their interaction were designated as fixed effects in the model with piglet nested in sow designated as a random effect. The effect of gender across treatments was examined using ANOVA to confirm that data from female piglets could be pooled to serve as a procedural control. Sow parity was also included as a covariate in the model. Where there was evidence of a treatment-by-time interaction (P<0.1), simple effect comparisons of LS means were conducted using the Tukey-Kramer adjustment for multiple comparisons. ADG outcomes best fit a Gaussian distribution. The effect of gender across treatments was also examined by ANOVA to clarify the effect of drug exposure from the effect of processing. For both outcomes, statistical significance was set a priori at P<0.05.

To account for the fact that not all the piglets were blood sampled at every time point due to blood volume restrictions in piglets, individual piglet peak cortisol concentrations (CortCmax) were calculated for each piglet after processing by visual inspection of the data. These data were also compared statistically using the same nonlinear mixed-effects analysis (PROC GLMMIX; SAS university edition v9.04.01, SAS Institute, Cary, N.C.) as previously described. Statistical significance of the CortCmax data was set a priori at P<0.05.

Results

Firocoxib Pharmacokinetics in Sows Following IM Administration

Figure 3:
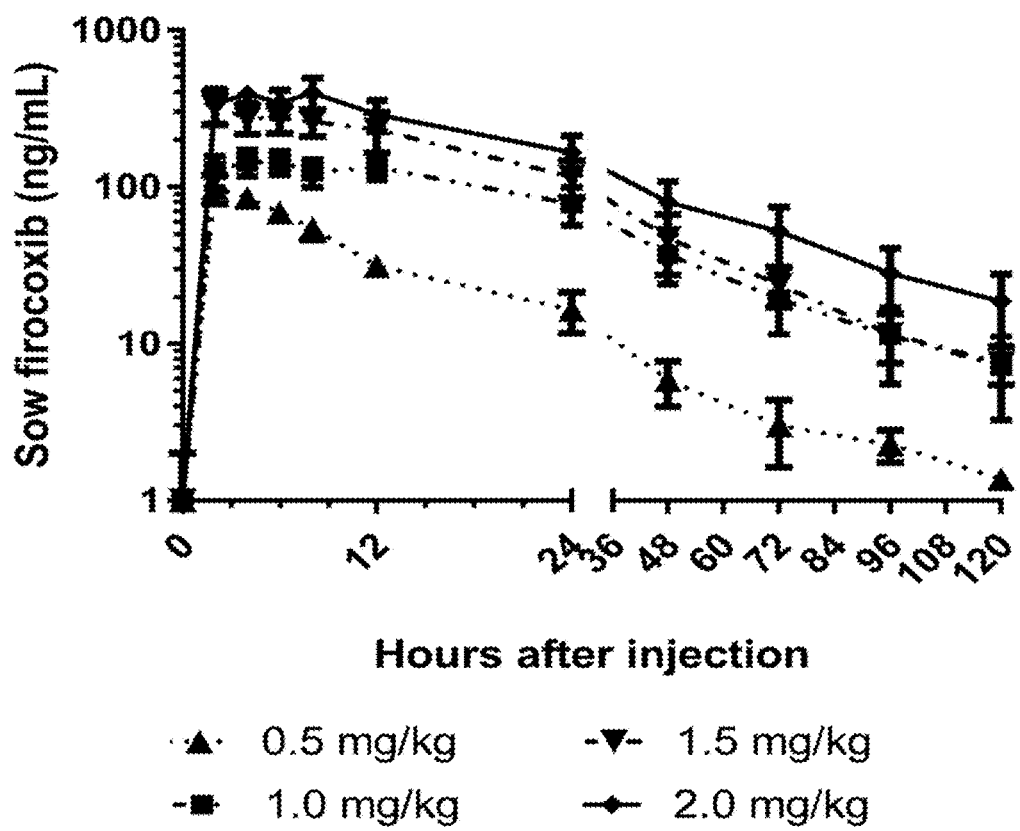
FIG. 3 is a graph of the mean (±SEM) plasma firocoxib concentrations (ng/mL) for lactating sows administered firocoxib via the intramuscular route at 0.5 mg/kg, 1.0 mg/kg, 1.5 mg/kg, or 2.0 mg/kg in Example 2.

The pharmacokinetic parameters for firocoxib following IM administration in sows is presented in FIG. 3 and Table 4. The mean±SEM plasma firocoxib concentrations in the sows from the four treatment groups that received a single IM dose of firocoxib at 0.5, 1.0, 1.5, or 2.0 mg/kg are presented in FIG. 3. The pharmacokinetic parameters for firocoxib in sows following IM administration are presented in Table 4. Mean±SEM firocoxib $C_{max}$ values of 107.90±15.18, 157.50±24.91, 343.68±78.89, and 452.83±90.27 ng/mL were recorded at 3.5, 5.5, 3.0, and 4.5 h, respectively, in sows receiving 0.5, 1.0, 1.5, or 2.0 mg/kg firocoxib. Mean $C_{max}$ was higher in sows that received 2.0 mg/kg compared to sows that received 1.0 mg/kg and 0.5 mg/kg (P=0.03). Mean AUC was also significantly lower in sows that received 0.5 mg/kg compared to sows that received 1.0 mg/kg, 1.5 mg/kg and 2.0 mg/kg (P=0.0304) respectively. Firocoxib demonstrated a prolonged plasma elimination half-life ($T_{1/2}\lambda z$) ranging from 26.71±5.77 h to 31.09±6.73 h.

Figure 4:
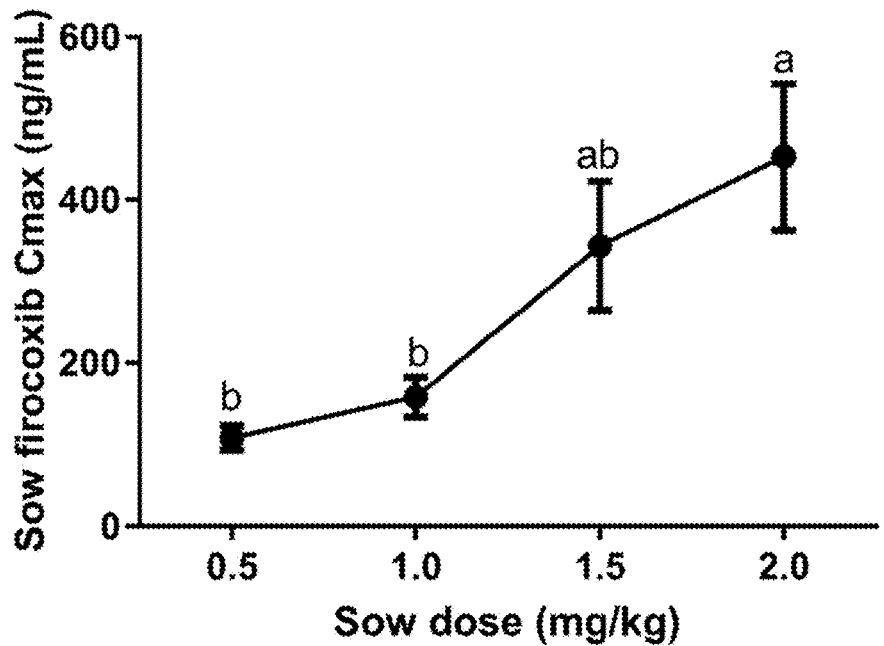
FIG. 4 is a graph of mean peak plasma firocoxib concentrations ($C_{max}$) between lactating sows administered firocoxib via the intramuscular route at 0.5 mg/kg, 1.0 mg/kg, 1.5 mg/kg, or 2.0 mg/kg (a-b: $p<0.05$).
Figure 5:
FIG. 5 is a graph of mean area under the plasma concentration vs. time curve (AUC) between lactating sows administered firocoxib via the intramuscular route at 0.5 mg/kg, 1.0 mg/kg, 1.5 mg/kg, or 2.0 mg/kg (a-b: $p<0.05$).

Dose linearity was investigated by plotting the $C_{max}$ (FIG. 4) and AUC (FIG. 5) values for firocoxib in sows against the injected doses. The results suggest that for both $C_{max}$ ($R^2$=0.60) and $AUC_{0\text{-}last}$ ($R^2$=0.55) the response was linear across the four doses that were investigated.

Based on these data it is apparent that the $C_{max}$ and AUC increased in a linear manner across the 4 doses that were investigated.

Firocoxib Pharmacokinetics in Piglets after Transmammary Delivery

Figure 6:
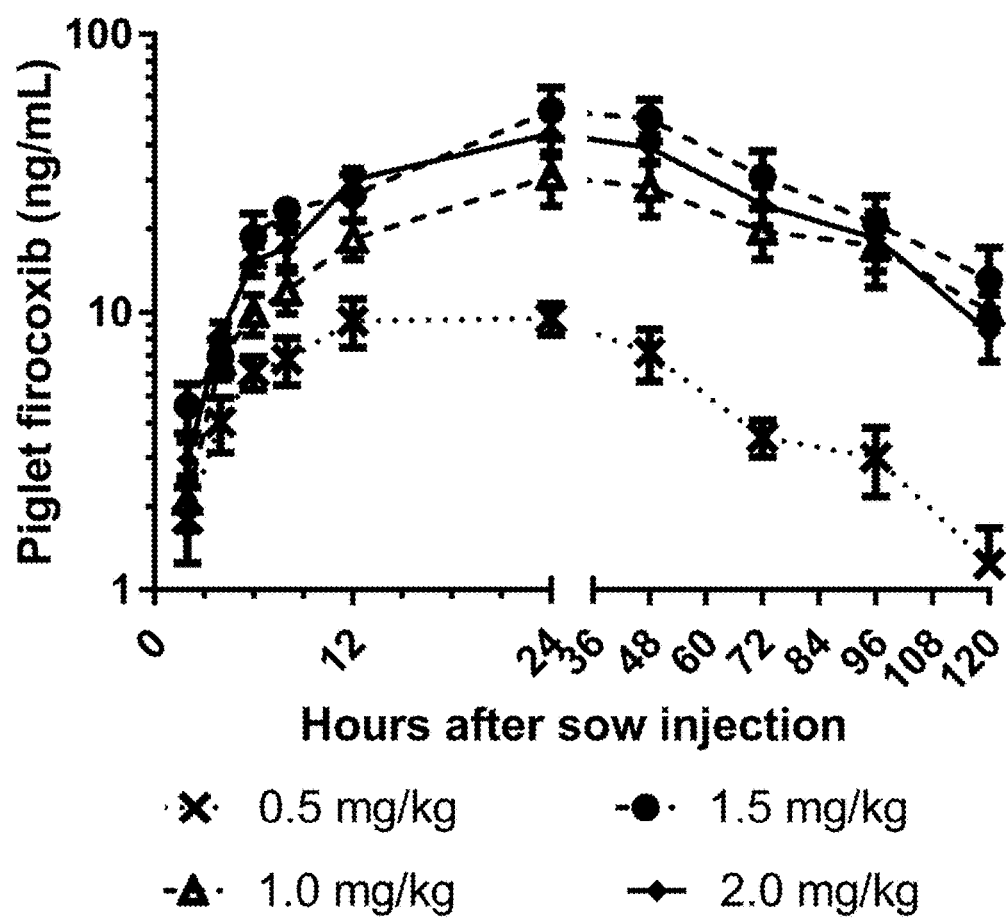
FIG. 6 is a graph comparing mean (±SEM) plasma firocoxib concentration (ng/mL) for piglets nursing lactating sows administered firocoxib at 0.5 mg/kg, 1.0 mg/kg, 1.5 mg/kg, or 2.0 mg/kg via intramuscular injection (n=12 piglets/treatment/time point).

The pharmacokinetic parameters for firocoxib following transmammary delivery to piglets is presented in FIG. 6 and Table 5.

Mean peak plasma firocoxib concentrations (Cmax) of 9.53 ng/mL, 31.04 ng/mL, 53.30 ng/mL and 44.03 ng/mL, was observed at 24 h after firocoxib was administered via injection to the sows. Firocoxib demonstrated a prolonged plasma elimination half-life of between 30.86 hours and 48.71 hours in piglets after transmammary delivery.

There was no effect of gender on plasma firocoxib concentrations over time (P=0.38), therefore data from male and female piglets were combined for subsequent pharmacokinetic analysis. The results for the plasma firocoxib concentrations (mean±SEM) in the piglets after the sows were injected with firocoxib (0.5, 1.0, 1.5, or 2.0 mg/kg) are presented in FIG. 6. The results for the pharmacokinetic parameters following transmammary delivery to the piglets are presented in Table 5.

TABLE 5

Pharmacokinetic parameters in piglets after transmammary delivery

| Sow Dose (IM) | | 0.5 mg/kg IM Piglet | 1.0 mg/kg IM Piglet | 1.5 mg/kg IM Piglet | 2.0 mg/kg IM Piglet |
|---|---|---|---|---|---|
| Parameter | Units | Mean | Mean | Mean | Mean |
| Cmax | ng/mL | 9.53 | 31.04 | 53.30 | 44.03 |
| Tmax | h | 24.00 | 24.00 | 24.00 | 24.00 |
| Lamda_Z | 1/h | 0.02 | 0.01 | 0.02 | 0.02 |
| Lamda_HL | h | 30.86 | 48.71 | 37.91 | 32.42 |
| $AUC_{last}$ | h * ng/mL | 635.36 | 2,468.00 | 3,897.55 | 3,220.90 |
| AUC∞ | h * ng/mL | 690.47 | 3,178.00 | 4,615.17 | 3,652.32 |
| AUC∞ extrpl | % | 0.08 | 0.22 | 0.16 | 0.12 |
| $AUMC_{last}$ | h * h * ng/mL | 28,443.00 | 136,805.00 | 204,246.00 | 166,016.00 |
| MRT last | h | 44.76 | 55.42 | 52.41 | 51.54 |
| AUC 0-24 h | h * ng/mL | 175.98 | 406.67 | 662.37 | 608.69 |

TABLE 4

Pharmacokinetic parameters in sows after IM administration

| Dose (IM) | | 0.5 mg/kg | | 1.0 mg/kg | | 1.5 mg/kg | | 2.0 mg/kg | |
|---|---|---|---|---|---|---|---|---|---|
| Parameter | Units | Mean | SEM | Mean | SEM | Mean | SEM | Mean | SEM |
| $\lambda_Z$ | 1/h | 0.03 | 0.006 | 0.03 | 0.002 | 0.02 | 0.003 | 0.02 | 0.002 |
| $T_{1/2}\lambda_Z$ | h | 28.87 | 6.92 | 26.70 | 2.88 | 29.89 | 4.84 | 31.09 | 3.36 |
| $T_{max}$ | h | 3.50 | 0.96 | 5.50 | 0.96 | 3.00 | 0.58 | 4.50 | 1.26 |
| $C_{max}$ | ng/mL | 107.90 | 15.18 | 157.50 | 24.91 | 343.68 | 78.89 | 452.83 | 90.27 |
| CL/F | L/h/kg | 0.33 | 0.04 | 0.21 | 0.05 | 0.19 | 0.03 | 0.18 | 0.04 |
| $AUC_{0\text{-}24h}$ | h × ng/mL | 1030 | 62 | 2673 | 0.486 | 4841 | 961 | 6639 | 1421 |
| $AUC_{0\text{-}last}$ | h × ng/mL | 1534 | 182 | 5331 | 1.357 | 8323 | 1814 | 12721 | 3548 |
| $AUC_{INF}$ | h × ng/mL | 1586 | 184 | 5624 | 1.534 | 8656 | 1760 | 13651 | 4045 |
| AUC_Exp | % | 3.39 | 0.66 | 4.15 | 1.50 | 4.98 | 2.92 | 5.61 | 1.83 |
| AUMC | $h^2$ × ng/mL | 31765 | 8530 | 164892 | 58409 | 215365 | 56451 | 392753 | 142492 |
| $MRT_{0\text{-}last}$ | h | 27.16 | 7.64 | 29.38 | 2.89 | 26.35 | 3.66 | 29.07 | 2.86 |
| $MRT_{INF}$ | h | 29.36 | 9.93 | 34.80 | 4.87 | 33.48 | 7.73 | 36.80 | 5.44 |
| $V_Z/F$ | L/kg | 13.82 | 4.25 | 7.82 | 1.44 | 9.12 | 3.24 | 7.75 | 1.55 |

TABLE 6

Pharmacokinetic parameters in nursing piglets

| Sow Dose (IM) | | 0.5 mg/kg | | 1.0 mg/kg | | 1.5 mg/kg | | 2.0 mg/kg | |
|---|---|---|---|---|---|---|---|---|---|
| Parameter | Units | Mean | SEM | Mean | SEM | Mean | SEM | Mean | SEM |
| $\lambda_Z$ | 1/h | 0.02 | | 0.01 | | 0.05 | | 0.02 | |
| $T_{1/2}\lambda_Z$ | h | 30.86 | | 48.71 | | 37.91 | | 32.42 | |
| $T_{max}$ | h | 24.00 | 12.56 | 24.00 | 14.83 | 24.00 | 14.17 | 24.00 | 12.21 |
| $C_{max}$ | ng/mL | 9.53 | 1.21 | 31.04 | 6.79 | 53.30 | 11.10 | 44.03 | 7.47 |
| $AUC_{0-24h}$ | h × ng/mL | 175.98 | | 406.67 | | 662.37 | | 608.69 | |
| $AUC_{0-last}$ | h × ng/mL | 635.36 | 55.82 | 2468.00 | 315.10 | 3897.55 | 459.80 | 3220.90 | 279.30 |
| $AUC_{INF}$ | h × ng/mL | 690.47 | | 3178.00 | | 4615.17 | | 3652.32 | |
| AUC_Exp | % | 0.08 | | 0.22 | | 0.16 | | 0.12 | |
| AUMC | $h^2$ × ng/mL | 28433.00 | | 136805.00 | | 204246.00 | | 166016.00 | |
| $MRT_{0-last}$ | h | 44.76 | | 55.42 | | 54.41 | | 51.54 | |

The plasma firocoxib concentration versus time profiles for the four groups of piglets were similar except that there was a more rapid decline in drug concentrations after $C_{max}$ in the piglets that nursed sows that received a 0.5 mg/kg dose. Mean peak plasma concentrations ($C_{max}$) of 9.53 ng/mL, 31.04 ng/mL, 53.30 ng/mL, and 44.03 ng/mL were found at 24 h after 0.5, 1.0, 1.5, or 2.0 mg/kg firocoxib administration via injection to the sows, respectively. Mean $C_{max}$ was lower in piglets nursing sows that received 0.5 mg/kg compared to piglets from sows that received 1.0 mg/kg (P=0.0012), 1.5 mg/kg (P<0.0001) and 2.0 mg/kg (P<0.0001). Furthermore, $C_{max}$ was significantly higher in piglets from sows that received 1.5 mg/kg compared to piglets from sows that received 1.0 mg/kg (P=0.0488). Mean AUC was also significantly lower in piglets from sows that received 0.5 mg/kg compared to piglets from sows that received 1.0 mg/kg (P=0.0003), 1.5 mg/kg (P<0.0001) and 2.0 mg/kg (P<0.0001) respectively. Firocoxib had a prolonged plasma $T_{1/2}\lambda z$ between 30.86 h and 48.71 h in the piglets after transmammary delivery.

Figure 7:
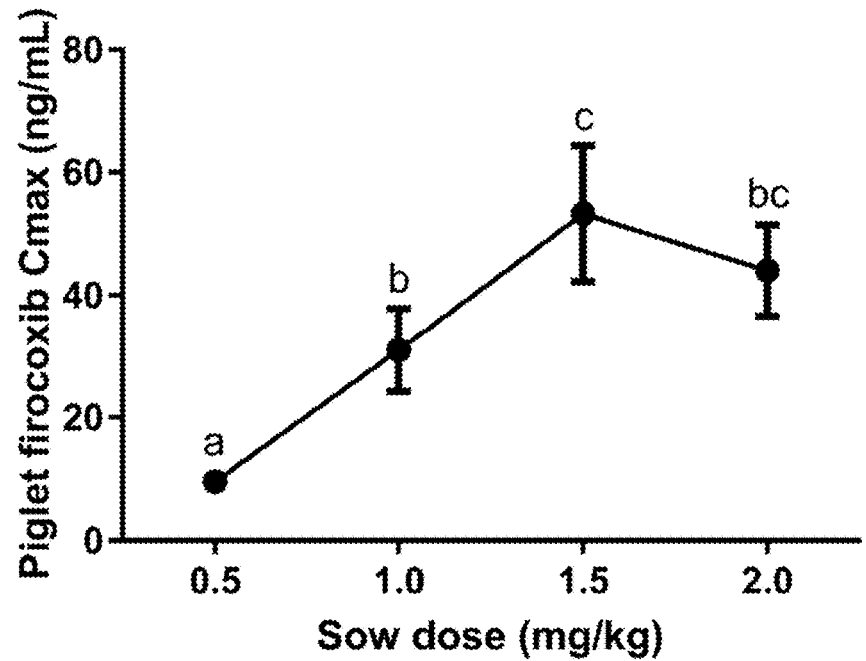
FIG. 7 is a graph of the mean peak plasma firocoxib concentrations ($C_{max}$) between piglets nursing lactating sows administered firocoxib at 0.5 mg/kg, 1.0 mg/kg, 1.5 mg/kg, or 2.0 mg/kg via intramuscular injection (a-c: $p<0.05$).

Dose linearity was investigated by plotting the $C_{max}$ (FIG. 7) and $AUC_{0-last}$ (FIG. 8) values against the administered doses. The results suggest that for both $C_{max}$ ($R^2$=0.23) and $AUC_{0-last}$ ($R^2$=0.21), dose linearity was absent in piglets across the four doses that were investigated.

Translactational Delivery of Firocoxib

Figure 9:
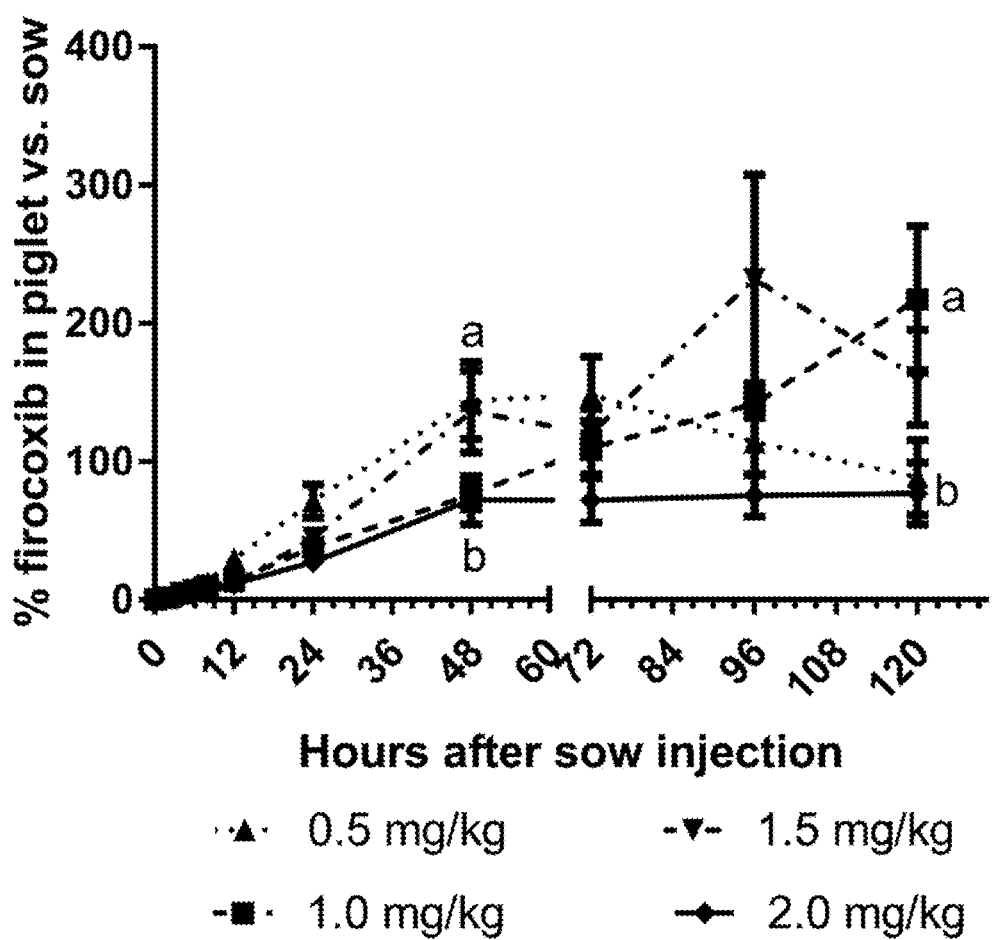
FIG. 9 is a graph comparing the plasma firocoxib concentration of nursing piglets as a percentage of the plasma firocoxib concentration in lactating sows administered firocoxib via the intramuscular route at 0.5 mg/kg, 1.0 mg/kg, 1.5 mg/kg, or 2.0 mg/kg (a-b: $p<0.05$).

The concentration of firocoxib in the plasma of the piglets as a percentage of the plasma firocoxib concentrations in the medicated sows at the same timepoint are illustrated in FIG. 9. There was evidence of a significant effect of treatment (P=0.0005), time (P<0.0001) and a time X treatment interaction (P<0.0001). Specifically, the concentration of firocoxib in the piglets as a percentage of the firocoxib in the sow at 48 hours was significantly greater in the sows that received 0.5 mg/kg and 1.5 mg/kg firocoxib compared to the other 2 groups (P<0.05). After 48 h, there was a plateau in the piglets who nursed on the sows that received the 2.0 mg/kg dose. At 120 h after drug administration via injection, the concentrations in the piglet plasma samples as a percentage of the concentrations in the sow plasma samples were significantly greater in the 1.0 mg/kg and 1.5 mg/kg groups, compared with the 0.5 mg/kg and 2.0 mg/kg groups.

Figure 8:
FIG. 8 is a graph of the mean area under the plasma concentration vs. time curve (AUC) between piglets nursing lactating sows administered firocoxib at 0.5 mg/kg, 1.0 mg/kg, 1.5 mg/kg, or 2.0 mg/kg via intramuscular injection (a-b: $p<0.05$).

Upon closer examination, there was an absence of dose linearity as assessed using $C_{max}$ (FIG. 7) and AUC (FIG. 8). These data suggest that the passage of firocoxib from the sow plasma into the milk is likely a saturable process. This implies that an increase in firocoxib dose to the sow above 1.5 mg/kg is unlikely to result in higher concentrations of firocoxib in the milk.

Comparison of the AUC for firocoxib in sows with the AUC for firocoxib in piglets is presented in Table 7. The total drug exposure following transmammary delivery of firocoxib from medicated sows to piglets across the four treatment groups ranged from 25.32% in piglets from sows that received 2.0 mg/kg to 46.83% in piglets from sows treated with 1.5 mg/kg.

Given that Area Under the plasma drug concentration Curve (AUC) represents total firocoxib exposure over time, an alternative approach to investigating the transmammary delivery of firocoxib from the sow to the piglets is to express the AUC for firocoxib in piglets as a percentage of the AUC for firocoxib in sows (Table 7).

TABLE 7

Total firocoxib exposure in piglets as a percentage after transmammary delivery

| Sow Dose | Parameter | Sow (h * ng/mL) | Piglet (h * ng/mL) | % Exposure |
|---|---|---|---|---|
| 0.5 mg/kg | $AUC_{last}$ | 1,534.00 | 635.36 | 41.42 |
| | AUC∞ | 1,587.00 | 690.47 | 43.51 |
| 1.0 mg/kg | $AUC_{last}$ | 5,332.00 | 2,468.00 | 46.29 |
| | AUC∞ | 5,625.00 | 3,178.00 | 56.50 |
| 1.5 mg/kg | $AUC_{last}$ | 8,323.00 | 3,897.50 | 46.83 |
| | AUC∞ | 8,657.00 | 4,615.20 | 53.31 |
| 2.0 mg/kg | $AUC_{last}$ | 12,722.00 | 3,220.90 | 25.32 |
| | AUC∞ | 13,652.00 | 3,652.32 | 26.75 |

Piglets nursing on sows administered 0.5 mg/kg to 1.5 mg/kg firocoxib as a single intramuscular injection received between 41% and 46% of the total sow firocoxib exposure based on the AUC calculated using the last timepoint. When AUC was extrapolated to infinity, piglets nursing on sows that received 0.5 mg/kg to 1.5 mg/kg were exposed to 43% to 56% of the firocoxib that sows were exposure to. In contrast, piglets nursing on sows that received 2 mg/kg of firocoxib IM were exposed to 25% of the firocoxib that sows were exposed to. These data confirm that 1.5 mg/kg of firocoxib is likely the optimal dose to be administered to sows via injection for transmammary delivery to piglets.

Plasma Cortisol Concentrations

Figure 10:
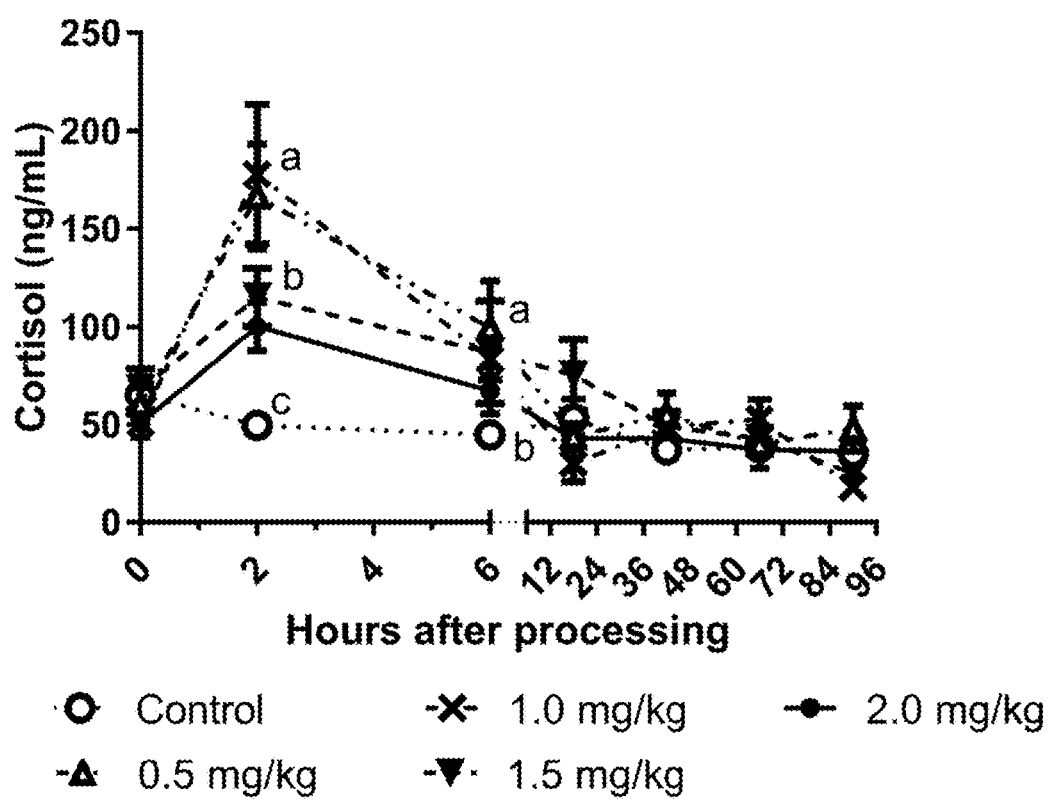
FIG. 10 is a graph comparing mean (±SEM) plasma cortisol concentrations (ng/mL) following processing in male piglets nursing lactating sows administered firocoxib at 0.5 mg/kg, 1.0 mg/kg, 1.5 mg/kg, or 2.0 mg/kg via intramuscular injection (n=8/time point/treatment), (a-c: $p<0.05$), each error bar is constructed using 1 standard error from the mean.

The plasma cortisol concentrations in the piglets were determined approximately 6 h after firocoxib was administered via injection to the sows (FIG. 10). This time point occurred immediately before castration, tail docking, and teeth clipping was performed in male piglets and was designated as T0 relative to processing. Cortisol concentrations from female piglets across treatment groups were not significantly different (P=0.36), therefore these data were pooled to comprise a procedural control group. The subsequent statistical analysis indicated that there were effects of treatment group (P=0.0003), time (P<0.0001), and a time-by-treatment interaction (P<0.0001) on plasma cortisol concentrations after castration, tail docking, and teeth clipping.

Prior to processing (T0), there was no difference in cortisol concentration between treatment groups. However, at 2±1 h after processing, plasma cortisol concentrations in processed male piglets was higher than female, procedural control, piglets (P<0.0002). Furthermore, at 2±1 h after processing, male piglets nursing sows that received 2.0 mg/kg firocoxib had lower mean plasma cortisol concentration compared with male piglets nursing sows that received 0.5 mg/kg (P=0.0397) and 1.0 mg/kg (P=0.0416) firocoxib. At 6±1 h after processing, higher plasma cortisol concentrations were recorded in male piglets from sows treated with 0.5 mg/kg (P=0.0017), 1.0 mg/kg (P=0.0078) and 1.5 mg/kg (P=0.0597) compared to female, procedural control, piglets.

Figure 11:
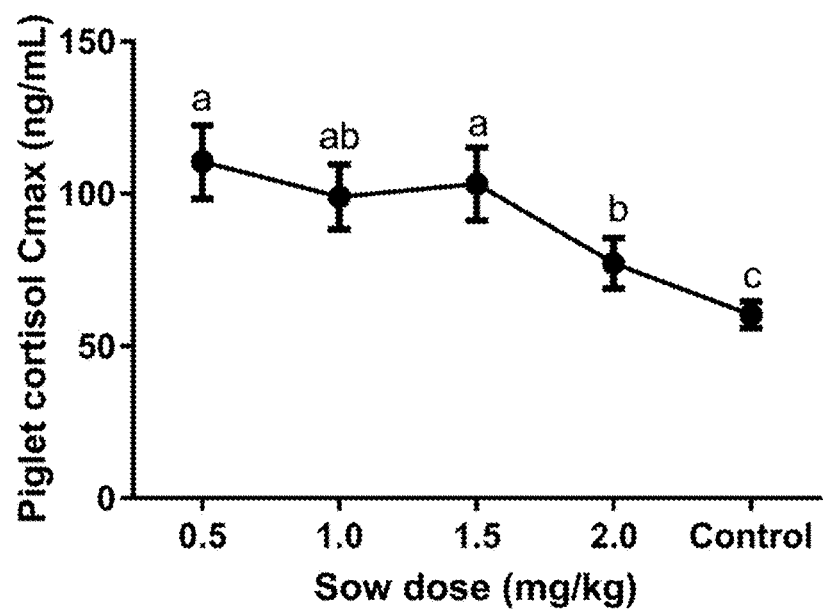
FIG. 11 is a graph of the mean peak plasma cortisol concentrations from individual piglets ($CortC_{max}$) after processing of male piglets nursing lactating sows administered firocoxib at 0.5 mg/kg, 1.0 mg/kg, 1.5 mg/kg, or 2.0 mg/kg via intramuscular injection. (a-c: $p<0.05$).

Analysis of the $CortC_{max}$ data revealed a significant treatment effect (P<0.0001) (FIG. 11). Specifically, maximum cortisol concentrations were greater in individual male piglets from sows in the 0.5 mg/kg firocoxib treatment group compared to piglets from sows that received 2.0 mg/kg firocoxib (P=0.014). Similarly, $CortC_{max}$ concentrations were higher in piglets from sows administered 1.5 mg/kg firocoxib compared to piglets from sow that received 2.0 mg/kg firocoxib (P=0.05) via injection. Processed male piglets across all treatment groups had significantly greater $CortC_{max}$ concentrations compared to unprocessed female piglets (P<0.044).

Piglet Average Daily Gain (ADG)

Figure 12:
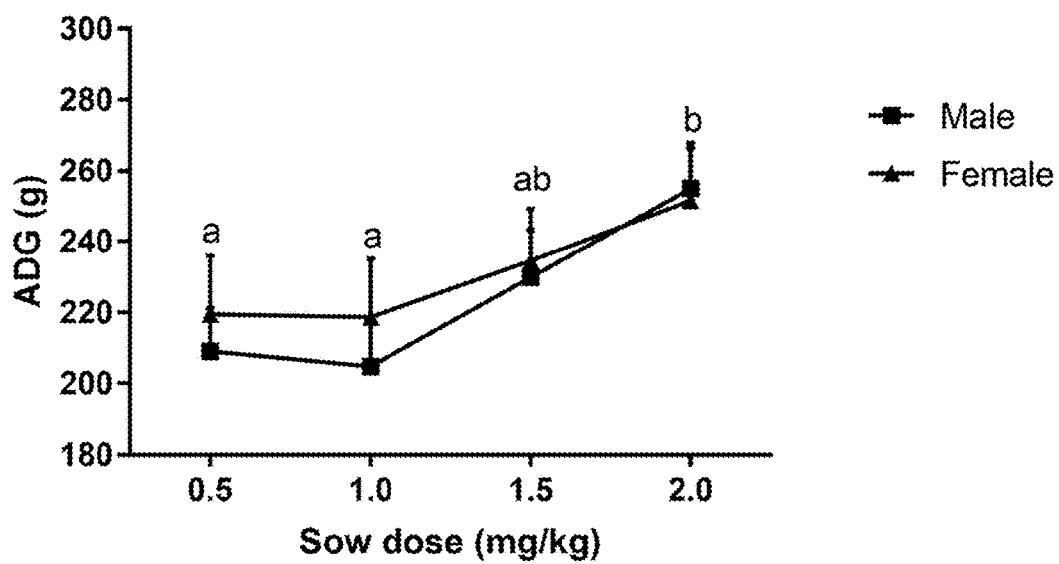
FIG. 12 is a bar graph comparing mean (±SEM) average daily weight gain (ADG) (g) at 21 d after processing of male piglets nursing sows administered firocoxib at 0.5 mg/kg (n=22), 1.0 mg/kg (n=21), 1.5 mg/kg (n=18), or 2.0 mg/kg (n=24) via intramuscular injection. (a-b: $p<0.05$).
Figure 13:
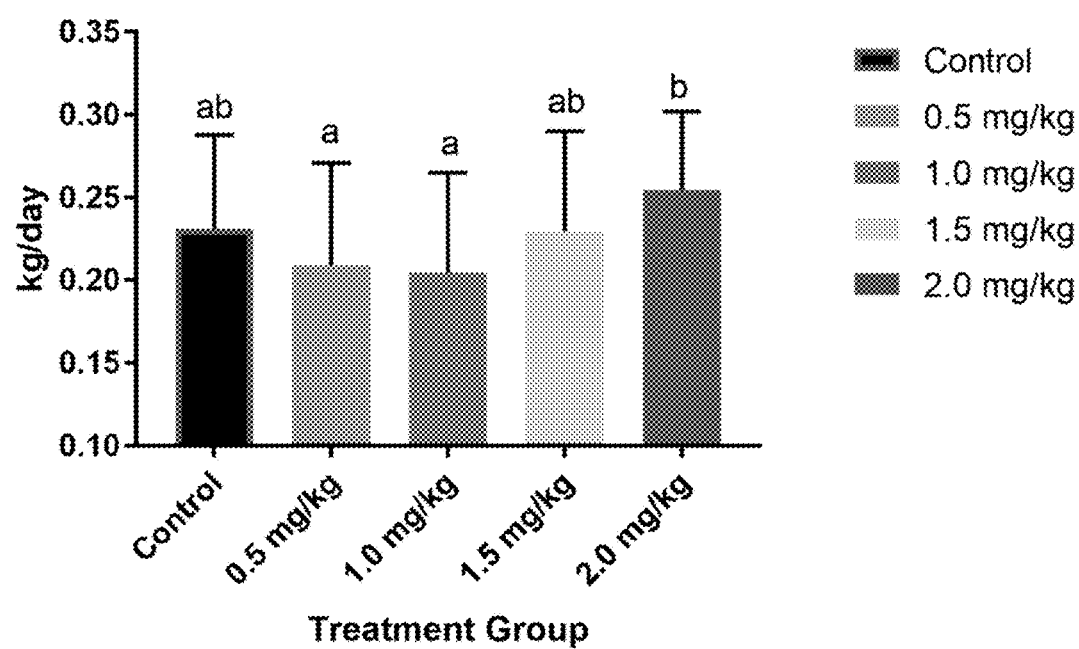
FIG. 13 is a bar graph of the mean average daily gain in the control group (female) or male piglets after processing.

Eight piglets died between processing and weaning. Average daily gain in body weight (ADG) of the surviving piglets over the 21 d from processing to weaning was calculated by subtracting the body weight at processing from the body weight at weaning and dividing the result by the days from processing to weaning (FIG. 12 and FIG. 13). ADG between male and female piglets was not significantly different (P=0.53) therefore these data were pooled for analysis. The results suggest that there was an effect of treatment on ADG over the 21 d from processing to weaning (P=0.0157). Specifically, ADG increased with the increasing doses of firocoxib administered to the lactating sows via injection. Piglets that consumed milk from sows that received 2.0 mg/kg firocoxib at 6 h before processing gained more weight than piglets that consumed milk from sows that received 0.5 mg/kg (P=0.0076) or 1.0 mg/kg (P=0.0047) firocoxib.

TABLE 8

Least square means comparison of average daily gain (ADG) Differences of Treatment Group Least Squares Means

| Treatment | | Average Daily Gain (ADG) | | |
|---|---|---|---|---|
| Treatment Group | Treatment Group | Mean Difference (g) | SEM | P-value |
| 0.5 mg/kg | 1.0 mg/kg | 2.56 | 14.54 | 0.860 |
| 0.5 mg/kg | 1.5 mg/kg | −17.98 | 14.29 | 0.211 |
| 0.5 mg/kg | 2.0 mg/kg | −39.01 | 14.37 | 0.008 |
| 1.0 mg/kg | 1.5 mg/kg | −20.54 | 14.35 | 0.155 |
| 1.0 mg/kg | 2.0 mg/kg | −41.57 | 14.43 | 0.005 |
| 1.5 mg/kg | 2.0 mg/kg | −21.03 | 14.18 | 0.141 |

Histopathology Examination of Tissues

No macroscopic lesions were evident on post-mortem examination of the kidney, liver, stomach and small intestines. Upon histological examination, all sections of liver and small intestine from lactating sows and nursing piglets across all 4 treatment groups were within normal limits (Tables 9 and 10). Ecstatic tubules, which are considered a congenital anomaly in swine, were observed in 5 sow and 10 piglet kidneys. These findings were not associated with higher firocoxib doses. Mild gastritis was observed in 19 sections of the stomach lining of the piglets but this finding is considered to be not specific for a singular etiology. No macroscopic or histological evidence of NSAID intoxication were observed in any planes of the sections of sow and piglet tissues examined.

TABLE 9

Histopathological findings in lactating sows at 21 d after intramuscular administration of firocoxib at 0.5 mg/kg, 1.0 mg/kg, 1.5 mg/kg, or 2.0 mg/kg.

| | | Treatment Group | | | |
|---|---|---|---|---|---|
| Tissue | Histopathology findings | 0.5 mg/kg | 1.0 mg/kg | 1.5 mg/kg | 2.0 mg/kg |
| Liver | Within normal limits | 4 | 4 | 4 | 4 |
| Small Intestine | Within normal limits | 4 | 4 | 4 | 4 |
| Kidney | Within normal limits | 1 | 1 | 3 | 1 |
| | Mild tubular ectasia | 1 | 2 | 1 | 1 |
| | Focal interstitial nephritis | 2 | 1 | 0 | 2 |
| Stomach | Within normal limits | 4 | 4 | 4 | 4 |

TABLE 10

Histopathological findings in nursing piglets (n = 48) at 21 d after intramuscular administration of firocoxib to lactating sows at 0.5 mg/kg, 1.0 mg/kg, 1.5 mg/kg, or 2.0 mg/kg.

| | | Treatment Groups | | | |
|---|---|---|---|---|---|
| Tissue | Histopathology findings | 0.5 mg/kg | 1.0 mg/kg | 1.5 mg/kg | 2.0 mg/kg |
| Liver | Within normal limits | 12 | 12 | 12 | 12 |
| Small Intestine | Within normal limits | 12 | 12 | 12 | 12 |
| Kidney | Within normal limits | 1 | 2 | 0 | 3 |
| | Rare tubular ectasia | 1 | 1 | 0 | 0 |
| | Mild tubular ectasia | 5 | 9 | 9 | 5 |
| | Moderate ectasia | 0 | 0 | 0 | 1 |
| | Prominent ectasia | 5 | 0 | 3 | 3 |
| Stomach | Within normal limits | 5 | 4 | 3 | 9 |
| | Mild vasculitis, muscle layer | 2 | 2 | 3 | 1 |
| | Mild gastritis | 5 | 6 | 6 | 2 |

Firocoxib and the Descyclopropylmethyl Metabolite Concentrations in Tissues

At 21 d after IM administration, no detectable concentrations of firocoxib or its descyclopropylmethyl metabolite were found in concentrations above the limit of quantitation (0.05 μg/g) in any of the muscle, liver, kidney, fat, or injection site tissue samples in sows. Similarly, there were no detectable concentrations of firocoxib in the tissues harvested from the piglets at weaning.

Discussion

To our knowledge, this is the first report examining the pharmacokinetics of firocoxib in swine. NSAIDs are the most commonly administered class of analgesic drugs in swine production systems in the United States due to their effectiveness, availability and relatively low cost. However, there are currently no analgesic drugs that have FDA-approved label indications for pain relief in pigs. Consumer concern about the welfare of farm animals experiencing pain during routine management procedures has increased efforts to develop effective, safe and practical analgesic protocols for use in piglets. Specifically, the "European Declaration on alternatives to surgical castration of pigs" required that from 1 Jan. 2012, surgical castration of pigs would only be performed with prolonged analgesia and/or anesthesia in all EU countries with the intent of phasing out the procedure by 2018. However, a 2015 survey of swine producers in 24 European countries found that only 5% of piglets received both anesthesia and analgesia and 41% of piglets received only analgesia at the time of surgical castration. In over 50% of the countries surveyed, (1) increased production costs; (2) the need for additional labor and (3) the lack of practical and effective analgesic/anesthetic protocols were identified as the primary factors that reduced compliance with the EU Declaration. The results of the present study suggest that a single injection of firocoxib administered to sows resulted in successful transmammary delivery of analgesia to nursing piglets prior to processing. This finding could potentially address many of the current impediments to routine analgesic drug use in piglets at the time of processing by reducing labor costs and improving piglet welfare through reduced stress. Furthermore, the cost of analgesia may be offset by enhanced production through increases in piglet weaning weights.

Plasma elimination half-life is the pharmacokinetic parameter that describes the time taken for the plasma drug concentrations to decrease by half. Firocoxib was found to have a long plasma elimination half-life in sows (26.7-31.1 h). A long terminal half-life is desirable from a clinical perspective because this may result in a longer duration of analgesia following a single dose that could reduce dosing frequency. In comparison to other commonly used NSAIDs in pigs, the elimination half-life of firocoxib in sows was approximately 10-fold longer than ketoprofen (3 h), 5-fold longer than meloxicam (6 h) and 4-fold longer than flunixin (7.5 h). These data support the hypothesis that firocoxib is a suitable analgesic for single dose injection in swine resulting in reduced labor costs and stress associated with frequent injections.

Volume of distribution is the pharmacokinetic measurement that describes the tendency of a drug to move from the blood into the tissues. Firocoxib was found to have a large volume of distribution (7.75-13.8 L/kg) in sows in the present study. A large volume of distribution is associated with high lipophilicity leading to greater distribution of a drug to tissues and body fluids. In comparison to other commonly used NSAIDs in pigs, the volume of distribution of firocoxib in sows was approximately 26-fold larger than flunixin (0.30 L/kg), 22-fold greater than ketoprofen (0.35 L/kg) and 18-fold greater than meloxicam (0.42 L/kg). These data suggest that firocoxib could be expected to have a greater tendency to distribute into the mammary gland and milk compared to other NSAIDs that demonstrate a smaller volume of distribution.

The results of the present study advance our understanding of transmammary delivery of analgesic compounds to manage pain in the offspring by expectedly demonstrating that this can be accomplished with a single injection into the sow using a dose volume that is attainable in a swine production environment.

The results of the pharmacokinetic analysis of the plasma firocoxib concentrations in the piglets indicate that the passage of firocoxib from the sow plasma into the milk was not linear. This suggests that transport across the blood-milk barrier may be a saturable process. Therefore, an increase in the sow dose above 1.5 mg/kg may not result in higher firocoxib concentrations in the milk. Furthermore, the AUC values represented total firocoxib exposure over time. Expressing the AUC values for firocoxib in piglets as a percentage of the AUC for firocoxib in sows is an alternative approach to investigation of the extent of the transmammary delivery of firocoxib from sows to piglets. Based on the AUC values calculated from 0 h to the last time point, piglets nursing on sows administered 0.5 mg/kg to 1.5 mg/kg firocoxib as a single IM injection received between 41% and 46% of the total sow firocoxib exposure. In contrast, the piglets nursing on sows that received 2.0 mg/kg firocoxib were exposed to 25% of the sow exposure. These results suggest that firocoxib doses above 2 mg/kg IM may not be associated with a proportional increase in drug transfer to nursing piglets.

Increased plasma cortisol concentrations are associated with stressful events such as those performed during processing. Specifically, assessment of the stress response using cortisol has been used as a proxy for measuring pain in livestock. However, an increase in plasma cortisol is not specific to any type of physical or mental stress. Routine animal handling procedures have been found to increase plasma cortisol concentrations in piglets. Specifically, a study comparing plasma cortisol concentrations of surgically castrated animals to sham-castrated animals found that animals that did not experience castration pain had lower peak cortisol concentrations and returned to baseline concentrations faster than surgically castrated animals. Persistent elevated plasma cortisol concentrations in the surgically castrated group could be a result of tissue damage or procedural pain. Until a pain-specific biomarker is identified and validated, the use of cortisol (with its limitations) as proxy measure for assessing pain in livestock will remain widespread in studies assessing the impact of production procedures and analgesic drugs on animal welfare.

In the present study, plasma cortisol concentrations reached a peak at approximately 30-60 min after the processing procedures in the piglets sampled at that time point. The time to peak plasma cortisol concentration and the magnitude of the response following processing procedures reported herein was similar to other reports. Furthermore, the results of the present study suggest that plasma cortisol concentrations in male piglets nursing sows that received the higher doses of firocoxib (1.5 mg/kg IM or 2.0 mg/kg IM), at 6 to 8 hours before processing, were lower compared with plasma cortisol concentrations in piglets nursing sows that received lower doses of firocoxib (0.5 mg/kg IM and 1.0 mg/kg IM). To account for the fact that not all piglets were sampled at this time point CortC$_{max}$ concentrations were compared. These further support the conclusion that piglets from sows that received 2.0 mg/kg of firocoxib tended to have a lower observed peak cortisol concentration. However, the observation of a dose dependent reduction in peak cortisol concentrations was less conclusive in this analysis because the actual C$_{max}$ may have occurred before or after the sparse sampling time point. To our knowledge, this is the first published report demonstrating that NSAID administration reduces plasma cortisol concentrations after processing in a dose-dependent manner. This finding supports the use of plasma cortisol as a surrogate biomarker of pain in dose-titration studies in swine.

Although it is recognized that NSAIDs do not mitigate the acute, incisional pain associated with castration, these results suggest that transmammary delivery of firocoxib administered to sows via injection at 1.5 mg/kg and 2.0 mg/kg reduces cortisol and therefore processing stress in piglets.

Interestingly, previous studies examining the impact of meloxicam or ketoprofen on growth rates when administered directly to piglets immediately before castration found no effects of NSAID administration on piglet average daily gain. However, these studies focused on the administration of the NSAID individually to each piglet at the time of processing. Therefore, one explanation for the beneficial effect of transmammary delivered firocoxib on piglet performance reported herein was that the directly-injected NSAID had a positive effect on material milk production and/or sow welfare, translating to a beneficial environment for the piglets. This hypothesis is supported by the observation that ADG increased in both male and female piglets in the present study regardless of processing status.

Specifically, parturition is generally associated with weight loss, reduced feed intake and an increase in stress, acute phase proteins and pain-related behaviors in sows. The negative impacts of parturition on sows may be mitigated by postpartum injection of an NSAID resulting in reduced weight loss, reduced lying times, and accordingly improved growth rates in piglets. The dose-dependent increase in ADG observed in the present study may have resulted from the beneficial effects of the NSAID, firocoxib, on postpartum physiology and behavior in the sows. Further studies focusing on changes in feed intake, bodyweight and milk composition of sows medicated with firocoxib are needed to elucidate if the NSAID improves the welfare of the sows in addition to impacting the welfare of the nursing piglets.

NSAID toxicity causes renal papillary necrosis which is considered a pathognomonic lesion for this condition. No evidence of NSAID toxicity was found on post-mortem examination of the kidney, liver, stomach and small intestines of the sows and piglets enrolled in the present study. Ecstatic tubules are considered a congenital anomaly in pigs. Gastric changes observed in the present study were considered mild and not specific for a singular etiology. Interstitial nephritis lesions in sow kidneys are considered an incidental finding. None of the histological changes that were reported were over-represented in any of the four treatment groups suggesting that these observations were not dose-dependent. Therefore, it is reasonable to conclude that firocoxib was safe for transmammary delivery from medicated sows to piglets at the doses that were tested.

Firocoxib administered to swine by any dose, route, for any duration or frequency constitutes extra-label drug use (ELDU) because currently there are no analgesic drugs specifically approved for pain management in pigs in the U.S. Under the Animal Medicinal Drug Use Clarification Act (AMDUCA), ELDU is permitted for relief of suffering in pigs provided specific conditions are met (AMDUCA, 1994). These conditions include that (1) ELDU is permitted only by or under the supervision of a veterinarian, (2) ELDU is allowed only for FDA-approved animal and human drugs, (3) ELDU is permitted only when the health of the animal is threatened and not for production purposes, (4) ELDU in feed is prohibited, and (5) ELDU is not permitted if this results in a violative food residue. In the present study, there were no detectable concentrations of firocoxib or its descyclopropylmethyl metabolite detected above the limit of quantitation (0.05 µg/g) for the assay in both sow and piglet tissues at 21 d after IM injection in the sow. In the EU, a maximum residue limit (MRL) of 10 µg/kg has been established in muscle and kidney, 15 µg/kg in fat and 60 µg/kg in the liver of horses (EMEA, 2006). Based on these data, tissue concentrations in the present study were well below the MRL for liver at 21 d after injection but the assay was not sensitive enough to quantify concentrations below the MRL for the other tissues, although none of these concentrations were above the limit of detection (0.01 µg/g) for the assay. Based on these data, additional studies conducted in accordance with FDA Guidance for Industry (GFI) #207 (Studies to Evaluate the Metabolism and Residue Kinetics of Veterinary Drugs In Food Producing Animals: Marker Residue Depletion Studies to Establish Product Withdrawal Periods) and GFI #3 (General Principles for Evaluating the Human Food Safety of New Animal Drugs Used in Food Producing Animals) are needed to characterize the tissue depletion of firocoxib after IM administration in sows.

The results of this study suggest that IM administration of firocoxib to sows at 7±1 h before performing piglet processing procedures resulted in successful transmammary drug delivery to the nursing piglets. Transmammary delivery of firocoxib resulted in a dose-dependent reduction of plasma cortisol concentrations after processing with piglets nursing sows that received 1.0 mg/kg and 2.0 mg/kg IM recording lower plasma cortisol concentrations than piglets nursing sows that received 1.5 mg/kg and 1.0 mg/kg IM. Furthermore, a dose-dependent increase in average daily gain was observed at 21 d after processing. Drug concentrations in tissue samples taken 21 d post-maternal injection were below the level of detection of the assay. When given via the transmammary route, firocoxib has potential as a therapeutic drug used for analgesia, to reduce processing-induced stress, improve piglet welfare, and enhance production through increases in weaning weights.

The invention claimed is:

1. A method for transmammary administration of an analgesic to an offspring swine, said method comprising:
    directly administering via injection a therapeutically effective amount of said analgesic to a lactating female swine to yield a treated lactating female swine; and
    allowing said offspring swine to obtain milk from said treated lactating female swine, wherein said analgesic is passed indirectly to the offspring swine through said milk of said treated lactating female swine,
    wherein said analgesic is a cyclooxygenase-2 inhibitor.

2. The method of claim 1, wherein said directly administering comprises a single injection of said analgesic into said lactating female swine.

3. The method of claim 1, wherein said analgesic is administered to said lactating female swine at a dosage of from about 0.5 mg/kg bodyweight to about 5 mg/kg bodyweight of said lactating female swine.

4. The method of claim 1, wherein said cyclooxygenase-2 inhibitor is selected from the group consisting of firocoxib, Celecoxib, Rofecoxib, valdecoxib, mavacoxib, cimicoxib, robenacoxib, deracoxib, pharmaceutically acceptable salts thereof, and combinations thereof.

5. The method of claim 1, wherein said analgesic is passed indirectly to the offspring swine through said milk about 6 hours after said directly administering.

6. The method of claim 1, wherein said analgesic accumulates in said milk to reach a therapeutically effective indirect dosage amount of said analgesic after about 6 hours after said injection.

7. The method of claim 1, wherein said therapeutically effective indirect dosage amount is achieved after only a single dosage form injection of said analgesic to said lactating swine.

8. A method of mitigating, inhibiting, and/or reducing pain in an offspring swine prior to undergoing processing procedures that would cause or result in pain, said method comprising:

directly administering via injection a therapeutically effective amount of an analgesic to a lactating female swine to yield a treated lactating female swine;

allowing said offspring swine to obtain milk from said treated lactating female animal, wherein said analgesic is passed indirectly to the offspring swine through said milk of said treated lactating female swine; and subjecting said offspring swine to said processing, wherein said analgesic is a cyclooxygenase-2 inhibitor.

9. The method of claim 8, wherein said offspring swine is allowed to obtain said milk from said lactating female swine at least about 6 hours prior to processing.

10. The method of claim 8, wherein said analgesic is administered to said lactating female swine up to about 12 hours before said processing.

11. The method of claim 8, wherein said offspring swine has a cortisol level that is lower than that of an offspring swine subjected to processing without obtaining milk from said treated lactating female swine.

12. The method of claim 8, wherein said offspring swine has a skin temperature that is lower than an offspring swine subjected to processing without obtaining milk from said treated lactating female swine.

13. The method of claim 8, wherein said offspring swine is subjected to said processing without the use of a local anesthetic or direct administration of analgesic to said offspring swine.

14. The method of claim 8, wherein said directly administering comprises a single injection of said analgesic into said lactating female swine.

15. The method of claim 8, wherein said analgesic is administered to said lactating female swine at a dosage of from about 0.5 mg/kg bodyweight to about 5 mg/kg bodyweight of said lactating female swine.

16. The method of claim 8, wherein said cyclooxygenase-2 inhibitor is selected from the group consisting of firocoxib, Celecoxib, Rofecoxib, valdecoxib, mavacoxib, cimicoxib, robenacoxib, deracoxib, pharmaceutically acceptable salts thereof, and combinations thereof.

17. The method of claim 8, wherein said analgesic is passed indirectly to the offspring swine through said milk about 6 hours after said directly administering.

18. The method of claim 8, wherein said analgesic accumulates in said milk to reach a therapeutically effective indirect dosage amount of said analgesic after about 6 hours after said directly administering.

19. The method of claim 8, wherein said therapeutically effective indirect dosage amount is achieved after only a single dosage form injection of said analgesic to said lactating swine.

20. The method of claim 8, wherein said offspring swine has increased average daily gain after said processing as compared to an offspring swine subjected to processing without obtaining milk from said treated lactating female swine.

21. The method of claim 8, wherein said analgesic is administered to said lactating female swine from about 0.5 h to 96 h prior to subjecting said offspring swine to said processing.

* * * * *